US 9,645,159 B2

(12) United States Patent
Pollack et al.

(10) Patent No.: US 9,645,159 B2
(45) Date of Patent: May 9, 2017

(54) TEST MENU EXPANSION SYSTEM AND METHOD

(71) Applicant: Siemens Healthcare Diagnostics Inc., Tarrytown, NY (US)

(72) Inventors: Benjamin S. Pollack, Budd Lake, NJ (US); Alexander Gelbman, Lake Worth, FL (US); Ryan German, Riverdale, NJ (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 0 days.

(21) Appl. No.: 14/760,279

(22) PCT Filed: Jan. 14, 2014

(86) PCT No.: PCT/US2014/011519
§ 371 (c)(1),
(2) Date: Jul. 10, 2015

(87) PCT Pub. No.: WO2014/110587
PCT Pub. Date: Jul. 17, 2014

(65) Prior Publication Data
US 2015/0355207 A1    Dec. 10, 2015

Related U.S. Application Data

(60) Provisional application No. 61/752,009, filed on Jan. 14, 2013.

(51) Int. Cl.
*G01N 33/10* (2006.01)
*G01N 33/02* (2006.01)
(Continued)

(52) U.S. Cl.
CPC ....... *G01N 35/021* (2013.01); *G01N 35/0092* (2013.01); *G01N 35/0095* (2013.01);
(Continued)

(58) Field of Classification Search
CPC ................ Y10T 436/00; Y10T 436/11; Y10T 436/114463; G01N 33/10; G01N 33/021;
(Continued)

(56) References Cited

U.S. PATENT DOCUMENTS

| 5,885,530 A | 3/1999 | Babson et al. |
| 7,182,912 B2 | 2/2007 | Carey et al. |

(Continued)

FOREIGN PATENT DOCUMENTS

| EP | 1 498 734 A1 | 1/2005 |
| EP | 2 023 150 A2 | 2/2009 |
| WO | 2010/059818 A1 | 5/2010 |

OTHER PUBLICATIONS

PCT International Search Report and Written Opinion dated Apr. 16, 2014 (17 Pages).

(Continued)

*Primary Examiner* — Christine T Mui

(57) ABSTRACT

An automation system for use with an in vitro diagnostics environment includes a track and a plurality of carriers configured to move along the track and hold one or more of a plurality of samples and one or more of a plurality of reagents having reagent types. The system also includes one or more testing stations, one or more local reagent storage areas located at or proximate to the one or more testing stations and one or more central reagent storage areas. The system further includes a control system configured to direct the one or more reagents from the one or more local reagent storage areas to the one or more testing stations based on received reagent information and direct the one or more reagents from the one or more central reagent storage areas to the one or more testing stations based on the received reagent information.

28 Claims, 13 Drawing Sheets

(51) Int. Cl.
*G01N 35/02* (2006.01)
*G01N 35/10* (2006.01)
*G01N 35/00* (2006.01)
*G01N 35/04* (2006.01)

(52) U.S. Cl.
CPC . *G01N 35/00663* (2013.01); *G01N 35/00722* (2013.01); *G01N 35/04* (2013.01); *G01N 35/10* (2013.01); *G01N 35/1002* (2013.01); *G01N 2035/0091* (2013.01); *G01N 2035/0094* (2013.01); *G01N 2035/00326* (2013.01); *G01N 2035/00673* (2013.01); *G01N 2035/0467* (2013.01); *Y10T 436/114165* (2015.01)

(58) Field of Classification Search
CPC .. G01N 33/02; G01N 33/00; G01N 33/00663; G01N 33/0613; G01N 33/000594; G01N 33/0584

USPC ............... 436/43, 50, 63; 422/50, 63, 43
See application file for complete search history.

(56) References Cited

U.S. PATENT DOCUMENTS

| | | | |
|---|---|---|---|
| 7,666,355 | B2 | 2/2010 | Alavie et al. |
| 7,855,077 | B2* | 12/2010 | Wilson ............... G01N 35/0099 422/510 |
| 8,012,768 | B2 | 9/2011 | Jafari et al. |
| 8,222,048 | B2 | 7/2012 | Fritchie et al. |
| 2005/0014272 | A1 | 1/2005 | Mizzer et al. |

OTHER PUBLICATIONS

Extended EP Search Report dated Jul. 25, 2016 of corresponding European Application No. 14737525.7, 4 Pages.

* cited by examiner

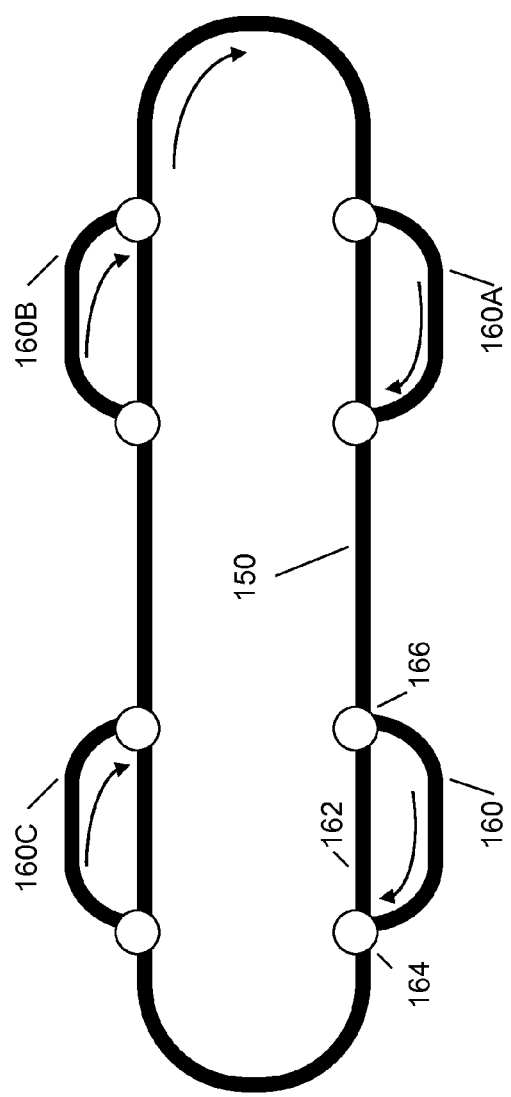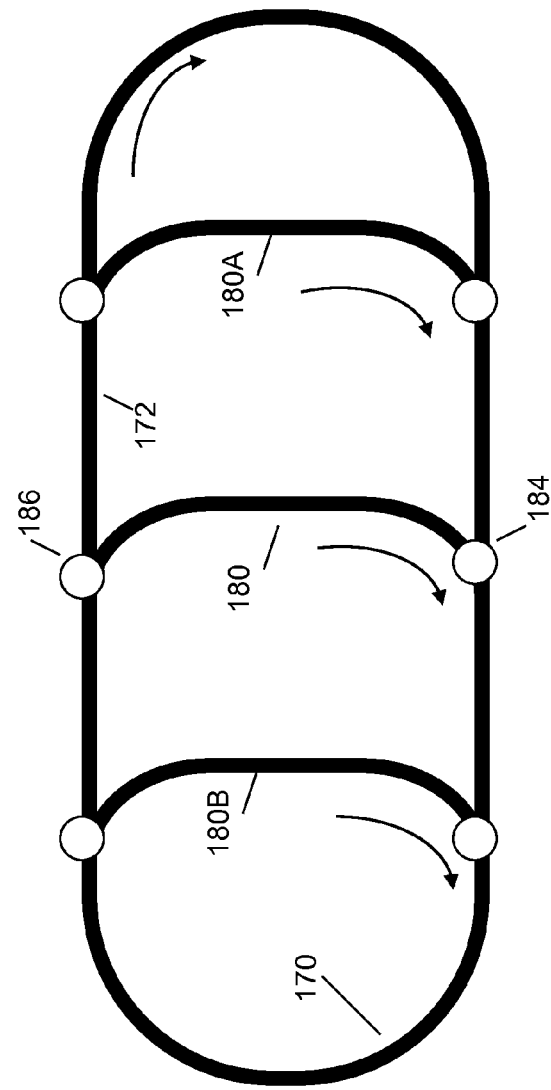

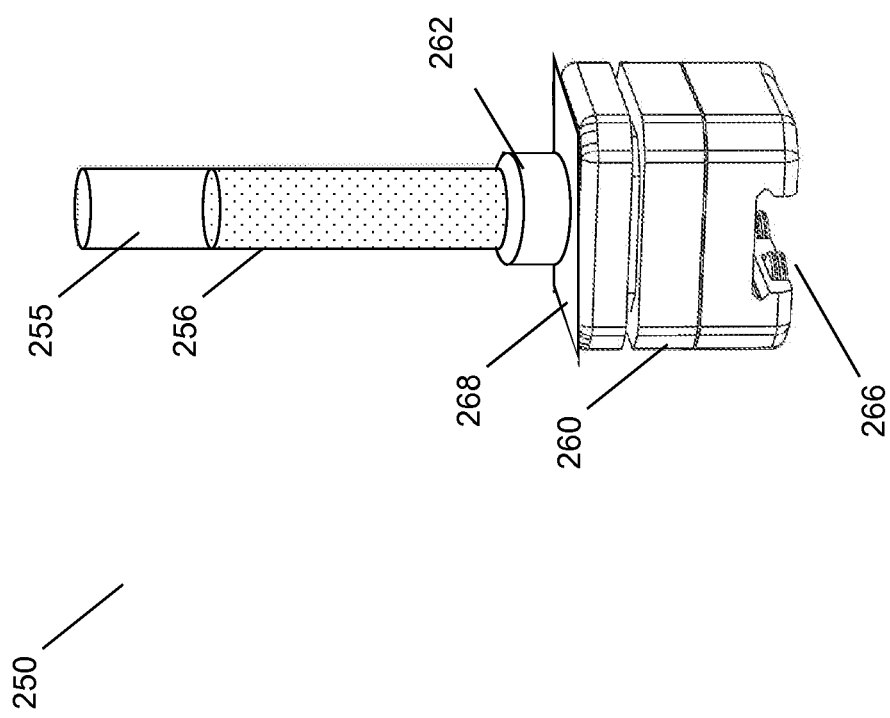

| Lab Size (#Tests / Day) | % of Test Menu Needed for 85% of Tests | % of Test Menu Needed for 90% of Tests | % of Test Menu Needed for 95% of Tests |
|---|---|---|---|
| Small (4757) | 22 | 28 | 39 |
| Medium (9013) | 21 | 27 | 32 |
| Large (13631) | 14 | 20 | 33 |

FIG. 7

TEST MENU EXPANSION SYSTEM AND METHOD

CROSS-REFERENCE TO RELATED APPLICATIONS

This application claims priority to U.S. provisional application Ser. No. 61/752,009 filed Jan. 14, 2013, which is incorporated herein by reference in its entirety.

TECHNOLOGY FIELD

The present invention relates in general to an automation system and method for use in a laboratory environment and, more particularly, to systems and methods that increase the test menu available to one or more clinical analyzers used for in vitro diagnostics.

BACKGROUND

In vitro diagnostics (IVD) allows labs to assist in the diagnosis of disease based on assays performed on patient fluid samples. IVD includes various types of analytical tests and assays related to patient diagnosis and therapy that can be performed by analysis of a liquid sample taken from a patient's bodily fluids, or abscesses. These assays are typically conducted with automated clinical chemistry analyzers (analyzers) onto which fluid containers, such as tubes or vials containing patient samples have been loaded. The analyzer extracts a liquid sample from the vial and combines the sample with various reagents in special reaction cuvettes or tubes (referred to generally as reaction vessels). In some conventional systems, a modular approach is used for analyzers. A lab automation system can shuttle samples between one sample processing module (module) and another module. Modules may include one or more stations, including sample handling stations and testing stations (e.g., a unit that can specialize in certain types of assays or can otherwise provide testing services to the larger analyzer), which may include immunoassay (IA) and clinical chemistry (CC) stations. Some traditional IVD automation track systems comprise systems that are designed to transport samples from one fully independent module to another standalone module. This allows different types of tests to be specialized in two different stations or allows two redundant stations to be linked to increase the volume of sample throughput available.

An individual test may require one or more unique reagents to be combined with a sample and some reagents may also be used for multiple tests. IVD reagent manufacturers typically offer a wide testing menu that includes a large number of possible tests (using one or more reagents) to cover a range of conditions. Conventional systems may, however, perform only a small subset of the tests available from the possible test menu because the physical space occupied by the reagent packs make it impractical to create an analyzer with enough storage space to hold every possible reagent. Conventional systems also typically store more than one pack for each frequently used reagent to increase walk away time. Accordingly, the amount of available space for storing a variety of types of reagents is decreased, thereby further reducing the number of tests that may be run from the available test menu.

Some conventional systems may use multiple analyzers and/or a larger number of modules and load different subsets of reagents on each analyzer and/or module. Increasing the number of analyzers and/or modules, however, may require some samples be sent to more than one analyzer and/or module to complete their respective tests, increasing turn-around time. Additional analyzers and/or modules may also impose additional cost, maintenance, and footprint on the system.

Other conventional systems utilize batch processing which includes loading different subsets (batches) of the available test menu at different times. While batch processing may increase the different amount of tests used from an available test menu, batch processing typically requires samples to be run on an analyzer multiple times to complete their respective tests, increasing the turn-around time and the labor costs by requiring system operators to manually load and unload the reagent packs for each batch at the different times.

SUMMARY

Embodiments of the present invention include an automation system for use with in vitro diagnostics that includes a track configured to provide one or more paths and a plurality of carriers configured to move along the track. Each of the plurality of carriers is configured to hold at least one of: (i) one or more of a plurality of samples; and (ii) one or more of a plurality of reagents having reagent types. The automation system also includes one or more testing station. Each testing station is configured to perform one or more tests by combining the one or more reagents with the one or more samples. The automation system also includes one or more local reagent storage areas located at or proximate to the one or more testing stations and configured to store the one or more reagents. The automation system also includes one or more central reagent storage areas configured to store the one or more reagents. The automation system also includes a control system configured to: (i) direct the one or more reagents from the one or more local reagent storage areas to the one or more testing stations based on received reagent information; and (ii) direct the one or more reagents from the one or more central reagent storage areas to the one or more testing stations based on the received reagent information.

According to one embodiment, the one or more local reagent storage areas are configured to store one or more common reagents of the plurality of reagents and the one or more central reagent storage areas configured to store one or more uncommon reagents of the plurality of reagents. The control system is further configured to: (i) direct the one or more common reagents from the one or more local reagent storage areas to the one or more testing stations to perform the one or more tests based on received reagent information; and (ii) direct the one or more uncommon reagents from the one or more central reagent storage areas to the one or more testing stations to perform the one or more tests based on the received reagent information.

According to another embodiment, the reagent information comprises scheduling information indicating at least one of: (i) an amount of the one or more reagent types scheduled to be combined with the one or more samples at one or more scheduled times; and (ii) an amount of the one or more reagent types scheduled to be combined with the one or more samples at the one or more testing stations.

In an aspect of an embodiment, the scheduling information is received via a laboratory information system.

In another aspect of an embodiment, the reagent information is received via a user interface.

In one embodiment, the control system is further configured to direct the one or more common reagents and the one or more uncommon reagents based on historical testing information.

In another embodiment, the control system is further configured to direct the one or more common reagents and the one or more uncommon reagents between: (i) the one or more local reagent storage areas; (ii) the one or more central reagent storage areas; and (iii) the testing stations to perform the one or more tests.

According to one embodiment, the control system is further configured to direct the one or more common reagents to the one or more central reagent storage areas prior to directing the one or more common reagents to the one or more testing stations.

According to another embodiment, the one or more local reagent storage areas include at least one long term local reagent storage area and the control system is further configured to direct the one or more of the plurality of reagents from the one or more central storage areas to the at least one long term local reagent storage area prior to directing the one or more reagents to the one or more testing stations.

In an aspect of an embodiment, the one or more local reagent storage areas include at least one short term local reagent storage area and the control system is further configured to direct one or more of the plurality of reagents from the one or more central storage areas to the at least one short term local reagent storage area prior to directing the one or more reagents to the one or more testing stations.

In one embodiment, groups of the plurality of reagents are stored in reagent type packs and the control system is further configured to: (i) direct one or more uncommon reagent type packs from the one or more central reagent storage areas to the one or more testing stations to perform the one or more tests based on the received reagent information; and (ii) direct the one or more uncommon reagent type packs having at least one uncommon reagent remaining in the respective one or more uncommon reagent type packs (a) back to the one or more central reagent storage areas after the one or more tests is performed or (b) to the one or more local reagent storage areas after the one or more tests is performed.

Embodiments of the present invention include an automation system having one or more pick and place devices for moving the plurality of samples and the plurality of reagents between: (i) the one or more local reagent storage areas; (ii) the one or more central reagent storage areas; (iii) the testing stations to perform the one or more tests; and (iv) the track.

According to an embodiment, the automation system further includes a reagent track configured to provide one or more reagent paths. The control system is further configured to: (i) direct the one or more samples along the track; and (ii) direct the one or more common reagent types and the one or more uncommon reagent types along the reagent track.

According to another embodiment, the automation system further includes one or more modules having at least one of: (i) the one or more testing stations; (ii) the one or more central storage areas; and (iii) the one or more local reagent storage areas.

In one aspect of an embodiment, the control system is further configured to direct one or more of the plurality of reagents based on the received reagent information indicating at least one of: (i) an amount of each type of common reagent stored at the one or more local reagent storage areas; (ii) an amount of each type of uncommon reagent stored at the one or more central storage areas; (iii) one or more locations of each type of common reagent on the track; and (iv) one or more locations of each type of uncommon reagent on the track.

In another aspect of an embodiment, the control system is further configured to direct one or more of the plurality of reagents based on testing information indicating which testing station is configured to perform the one or more tests.

In one embodiment, one or more of the plurality of reagent types are stored in reagent packs and the control system is further configured to remove one or more empty reagent packs from the track.

In another embodiment, one or more of the plurality of reagent types are stored in reagent packs and the control system is further configured to direct empty packs from the one or more local reagent storage areas to the one or more central reagent storage areas.

Embodiments of the present invention include an automation system for use with in vitro diagnostics that includes a plurality of analyzers. One or more of the plurality of analyzers includes a track configured to provide one or more path and a plurality of carriers configured to move along the track, each of the plurality of carriers configured to hold at least one of: (i) one or more of a plurality of samples; and (ii) one or more of a plurality of reagents having reagent types. The one or more analyzers also includes one or more local modules including one or more testing stations configured to perform one or more tests by combining the one or more reagents with the one or more samples and one or more local reagent storage areas located at or proximate to the one or more testing stations and configured to store one or more common reagents of the plurality of reagents. The one or more analyzers further includes one or more central modules comprising one or more central reagent storage areas configured to store one or more uncommon reagents of the plurality of reagents. The automation system also includes a control system configured to: (i) direct the one or more common reagents from the one or more local reagent storage areas of each respective analyzer to the one or more testing stations of each respective analyzer to perform the one or more tests based on reagent information; and (ii) direct the one or more uncommon reagents from the one or more central reagent storage areas of each respective analyzer to the one or more testing stations of each respective analyzer to perform the one or more tests based on the reagent information.

According to an embodiment, the control system is configured to direct the one or more common reagents and the one or more uncommon reagents based on the reagent information received from at least one of: (i) one or more of the plurality of analyzers; (ii) the one or more local modules; (iii) the one or more central modules; and (iv) one or more of the plurality of carriers.

According to an embodiment, the automation system further includes a scheduling information storage device configured to store the reagent information indicating at least one of: (i) an amount of the one or more reagent types scheduled to be combined with the one or more samples at one or more scheduled times; and (ii) an amount of the one or more reagent types scheduled to be combined with the one or more samples at the one or more testing stations. The control system is configured to direct the one or more common reagents and the one or more uncommon reagents based on the stored reagent information.

In one embodiment, the automation system further includes one or more calibration systems configured to calibrate the one or more common reagents and the one or more uncommon reagents. The control system is further configured to direct the one or more common reagents and the one or more uncommon reagents be calibrated by the one or more calibration systems at a predetermined time prior to their scheduled testing.

In another embodiment, one or more of the plurality of analyzers includes a connecting track portion which connects the tracks of the one or more analyzers and the control system is further configured to direct the one or more common reagents and the one or more uncommon reagents between the one or more analyzers.

Embodiments of the present invention include a method for operating an in vitro diagnostics system that includes storing one or more common reagents of a plurality of reagents at one or more local reagent storage areas located at or proximate to one or more testing stations and storing one or more uncommon reagents of the plurality of reagents at one or more central reagent storage areas. the method also includes receiving information used to determine at least one testing time at the one or more testing stations for one or more of the plurality of reagents to be combined with one or more samples and directing the one or more common reagents from the one or more local reagent storage areas to the one or more testing stations based on the received information. The method further includes directing the one or more uncommon reagents from the one or more central reagent storage areas to the one or more testing stations based on the received information and performing at least one test at the one or more testing stations by combining at least one of: (i) the one or more common reagents with the one or more samples; and (ii) the one or more uncommon reagents with the one or more samples.

According to an embodiment, the receiving information used to determine at least one testing time includes receiving scheduling information indicating of at least one of: (i) one or more reagent types scheduled to be combined with the one or more samples at the at least one scheduled testing time; and (ii) an amount of the one or more reagent types scheduled to be combined with the one or more samples at the at least one testing time.

According to another embodiment, the receiving information used to determine at least one testing time includes receiving historical testing information.

In one embodiment, the receiving information used to determine at least one testing time includes receiving reagent information indicating at least one of: (i) an amount of each type of common reagent stored at the one or more local reagent storage areas; and (ii) an amount of each type of uncommon reagent stored at the one or more central storage areas.

In another embodiment, the method further includes directing the one or more uncommon reagents from the one or more central storage areas to the one or more local reagent storage areas prior to directing the one or more uncommon reagents to the one or more testing stations.

In another embodiment, the method further includes directing the one or more common reagents to the one or more central reagent storage areas prior to directing the one or more common reagents to the one or more testing stations.

BRIEF DESCRIPTION OF THE DRAWINGS

The foregoing and other aspects of the present invention are best understood from the following detailed description when read in connection with the accompanying drawings. For the purpose of illustrating the invention, there is shown in the drawings embodiments that are presently preferred, it being understood, however, that the invention is not limited to the specific instrumentalities disclosed. Included in the drawings are the following Figures:

FIG. 2A and FIG. 2B are diagrammatic views of track geometries that can be used with the automation system embodiments disclosed herein;

FIG. 4A is a perspective view of an exemplary carrier that can be used with the embodiments disclosed herein;

FIG. 7 is a table illustrating percentages of an available test menu used by different sized labs to perform different percentage of each lab's tests that can be used with the embodiments disclosed herein;

DETAILED DESCRIPTION OF ILLUSTRATIVE EMBODIMENTS

Figure 1:
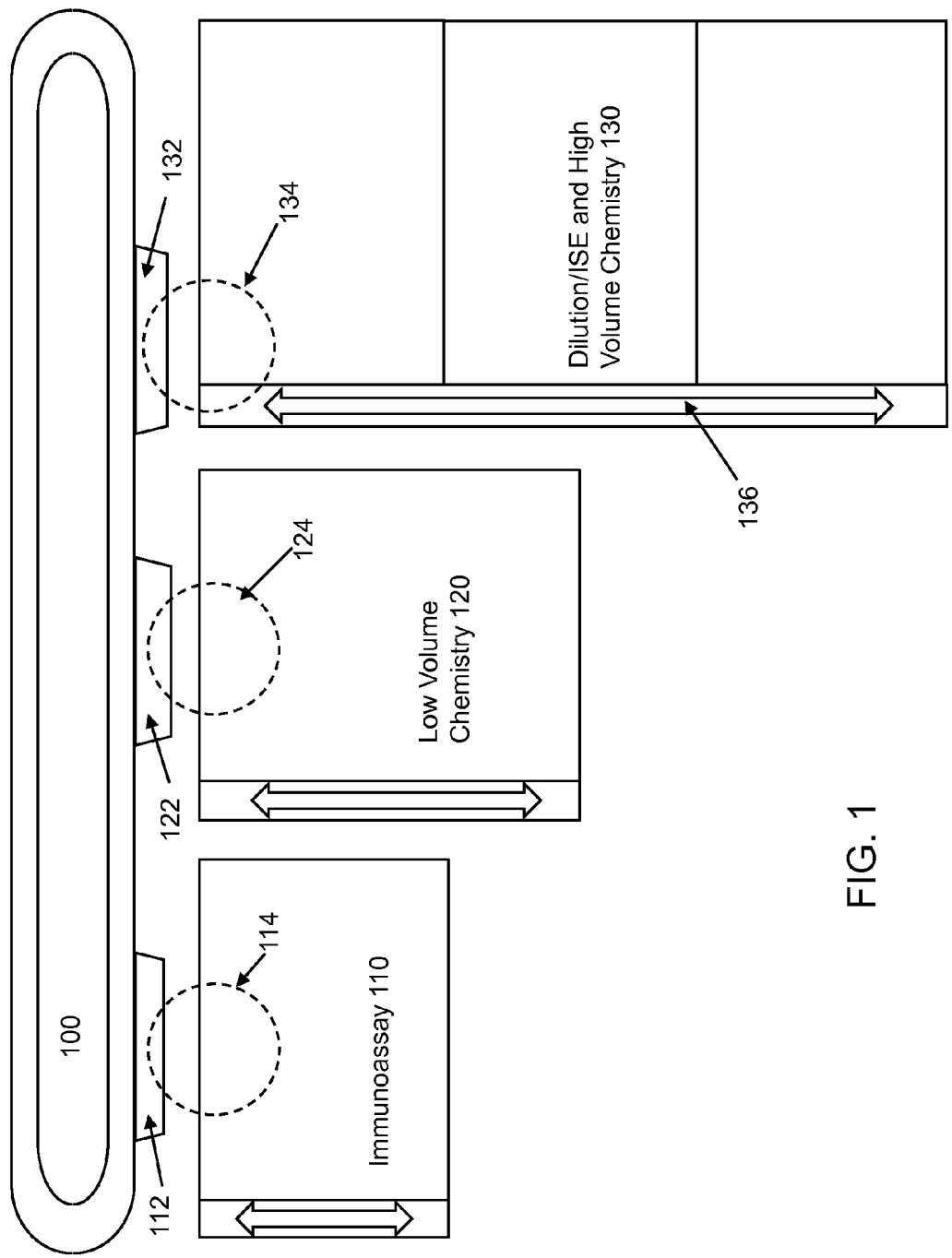
FIG. 1 is a top view of an exemplary clinical analyzer geometry that can be improved by use of the automation system embodiments disclosed.

Terms and Concepts Associated with Some Embodiments

Analyzer: Automated clinical analyzers ("analyzers") include clinical chemistry analyzers, automated immunoassay analyzers, or any other type of in vitro diagnostics (IVD) testing analyzers. Generally, an analyzer performs a series of automated IVD tests on a plurality of patient samples. Patient samples may be loaded into an analyzer (manually or via an automation system), which can then perform one or more immunoassays, chemistry tests, or other observable tests on each sample. The term analyzer may refer to, but is not limited to, an analyzer that is configured as a modular analytical system. A modular analytical system includes an integrated and extendable system comprising any combinations of a plurality of modules (which can include the same type of module or different types of modules) interconnected in a linear or other geometric configuration by an automation surface, such as an automation track. In some embodiments, the automation track may be configured as an integral conveyance system on which independent carriers are used to move patient samples and other types of material between the modules. Generally, at least one module in a modular analytical system is an analyzer module. Modules may be specialized or made redundant to allow higher throughput of analytical tasks on patient samples.

Analyzer module: An analyzer module is a module within a modular analyzer that is configured to perform IVD tests, such as immunoassays, chemistry tests, or other observable tests on patient samples. Typically, an analyzer module extracts a liquid sample from a sample vessel and combines the sample with reagents in reaction cuvettes or tubes (referred to generally as reaction vessels). Tests available in an analyzer module may include, but are not limited to, a subset of electrolyte, renal or liver function, metabolic, cardiac, mineral, blood disorder, drug, immunoassay, or other tests. In some systems, analyzer modules may be specialized or made redundant to allow higher throughput. The functions of an analyzer module may also be performed by standalone analyzers that do not utilize a modular approach.

Carrier: A carrier is a transportation unit that can be used to move sample vessels (and, by extension, fluid samples) or other items in an automation system. In some embodiments, carriers may be simple, like traditional automation pucks (e.g., passive devices comprising a holder for engaging a tube or item, a friction surface to allow an external conveyor belt in the automation track to provide motive force, and a plurality of sides that allow the puck to be guided by walls or rails in the automation track to allow the track to route a puck to its destination). In some embodiments, carriers may include active components, such as processors, motion systems, guidance systems, sensors, and the like. In some embodiments, carriers can include onboard intelligence that allows carriers to be self-guided between points in an automation system. In some embodiments, carriers can include onboard components that provide motive forces while, in others, motive forces may be provided by an automation surface, such as a track. In some embodiments, carriers move along automation tracks that restrict motion to a single direction (e.g., fore and aft) between decision points. Carriers may be specialized to a given payload in an IVD environment, such as having a tube holder to engage and carry a sample tube, or may include mounting surfaces suitable to carry different items around an automation system. Carriers can be configured to include one or more slots (e.g., a carrier may hold one or a plurality of sample vessels).

Central controller or processor: A central controller/processor (which may sometimes be referred to as a central scheduler) is a processor that is part of the automation system, separate from any processors onboard carriers. A central controller can facilitate traffic direction, scheduling, and task management for carriers. In some embodiments, a central controller can communicate with subsystems in the automation system and wirelessly communicate with carriers. This may also include sending trajectory or navigational information or instructions to carriers and determining which carriers should go where and when. In some embodiments, local processors may be responsible for managing carriers on local track sections, such as managing local queues. These local processors may act as local equivalents to central controllers.

Decision point: Decision points are points on an automation track where different navigational or trajectory decisions may be made for different carriers. A common example includes a fork in a track. One carrier may proceed without turning, while another may slow down and turn. Decision points may include stopping points at instruments, where some carriers may stop, while others may proceed. In some embodiments, deceleration zones ahead of turns may act as decision points, allowing carriers that will be turning to slow down to limit lateral forces, while others may proceed if not turning or if the motion profile for that carrier does not require slowing down. The decisions made at decision points can be made by processors onboard carriers, processors local to the track section, a central processor, or any combination thereof, depending on the embodiment.

Independent carrier: In some embodiments, carriers may be characterized as independently controlled carriers. Independently controlled carriers, are carriers with independently controlled trajectories. In some embodiments, independent carriers may be operating at the same time, on the same track, with carriers carrying one or a plurality of combinations of payloads that differ by size, weight, form factor, and/or content. The trajectories of each independently controlled carrier may be limited by a motion profile that includes maximum jerk, acceleration, direction, and/or speed for the carrier while moving in the automation system. The motion profile can limit or define the trajectory for each carrier independently. In some embodiments, a motion profile can be different for different sections of the automation system (e.g., in straight track sections vs. around curves to account for the added lateral forces while turning), for different carrier states (e.g., an empty carrier may have a different motion profile from a carrier transporting a sample or from a carrier transporting a reagent or other item), and/or for different carriers. In some embodiments, carriers can include onboard propulsion components that allow individual carriers to independently operate responsive to a motion profile or trajectory or destination instructions intended for each separate carrier.

Intelligent carrier/semi-autonomous carriers: In some embodiments, carriers may be characterized as intelligent carriers. An intelligent carrier is a carrier with onboard circuits that participates in motion, routing, or trajectory decisions. An intelligent carrier can include digital processors that execute software instructions to proceed along an automation surface responsive to the instructions or onboard analog circuits that respond to motion input (e.g., line follower circuits). Instructions may include instructions characterizing motion profiles, traffic, or trajectory rules. Some intelligent carriers may also include onboard sensors to assist onboard processors to route the carrier or make decisions responsive to the carrier's environment. Some intelligent carriers may include onboard components, such as motors or magnets, which allow the carrier to move responsive to control of an onboard processor.

In vitro diagnostics (IVD): In vitro diagnostics (IVD) are tests that can detect diseases, conditions, infections, metabolic markers, or quantify various constituents of bodily materials/fluids. These tests are performed in laboratory, hospital, physician office, or other health professional settings, outside the body of a patient. IVD testing generally utilizes medical devices intended to perform diagnoses from assays in a test tube or other sample vessel or, more generally, in a controlled environment outside a living organism. IVD includes testing and diagnosis of disease or quantifying various constituents of bodily materials/fluids based on assays performed on patient fluid samples. IVD includes various types of analytical tests and assays related to patient diagnosis and therapy that can be performed by analysis of a liquid sample taken from a patient's bodily fluids, or abscesses. These assays are typically conducted with analyzers into which tubes or vials containing patient samples have been loaded. IVD can refer to any subset of the IVD functionality described herein.

Landmarks: In embodiments where carriers include onboard sensors, optical or other marks in track surfaces or locations viewable/sensible from track surfaces can act as landmarks. Landmarks can convey geographic information to carriers, such as a current location, upcoming stopping location, decision point, turn, acceleration/deceleration points, and the like.

Lab automation system: Lab automation systems include any systems that can automatically (e.g., at the request of an operator or software) shuttle sample vessels or other items within a laboratory environment. With respect to analyzers, an automation system may automatically move vessels or other items to, from, amongst, or between stations in an analyzer. These stations may include, but are not limited to, modular testing stations (e.g., a unit that can specialize in certain types of assays or can otherwise provide testing services to the larger analyzer), sample handling stations, storage stations, or work cells.

Module: A module performs specific task(s) or function(s) within a modular analytical system. Examples of modules may include: a pre-analytic module, which prepares a sample for analytic testing, (e.g., a decapper module, which removes a cap on top of a sample test tube); an analyzer module, which extracts a portion of a sample and performs tests or assays; a post-analytic module, which prepares a sample for storage after analytic testing (e.g., a recapper module, which reseals a sample test tube); or a sample handling module. The function of a sample handling module may include managing sample containers/vessels for the purposes of inventory management, sorting, moving them onto or off of an automation track (which may include an integral conveyance system, moving sample containers/vessels onto or off of a separate laboratory automation track, and moving sample containers/vessels into or out of trays, racks, carriers, pucks, and/or storage locations.

Payload: While exemplary carriers are described with respect to carrying patient samples, in some embodiments, carriers can be used to transport any other reasonable payload across an automation system. This may include fluids, fluid containers, reagents, waste, disposable items, parts, or any other suitable payloads.

Processor: A processor may refer to one or more processors and/or related software and processing circuits. This may include single or multicore processors, single or multiple processors, embedded systems, or distributed processing architectures, as appropriate, for implementing the recited processing function in each embodiment.

Pullouts, sidecars, offshoot paths: These terms may be used to refer to track sections that are off the main portion of a track system. Pullouts or sidecars may include chords, parallel tracks, or other suitable means for separating some carriers from a primary traffic pattern. Pullouts or sidecars may be configured to facilitate physical queues or allow certain carriers to stop or slow down without disrupting traffic on a main track section.

Samples: Samples refers to fluid or other samples taken from a patient (human or animal) and may include blood, urine, hematocrit, amniotic fluid, or any other fluid suitable for performing assays or tests upon. Samples may sometimes refer to calibration fluids or other fluids used to assist an analyzer in processing other patient samples.

STAT (short turnaround time) sample: Samples may have different priority assigned by a laboratory information system (LIS) or operator to assign STAT priority to samples that should take precedent over non-STAT samples in the analyzer. When used judiciously, this may allow certain samples to move through the testing process faster than other samples, allowing physicians or other practitioners to receive testing results quickly.

Station: A station includes a portion of a module that performs a specific task within a module. For example, the pipetting station associated with an analyzer module may be used to pipette sample fluid out of sample containers/vessels being carried by carriers on an integrated conveyance system or a laboratory automation system. Each module can include one or more stations that add functionality to a module.

Station/module: A station includes a portion of an analyzer that performs a specific task within an analyzer. For example, a capper/decapper station may remove and replace caps from sample vessels; a testing station can extract a portion of a sample and perform tests or assays; a sample handling station can manage sample vessels, moving them onto or off of an automation track, and moving sample vessels into or out of storage locations or trays. Stations may be modular, allowing stations to be added to a larger analyzer. Each module can include one or more stations that add functionality to an analyzer, which may be comprised of one or more modules. In some embodiments, modules may include portions of, or be separate from, an automation system that may link a plurality of modules and/or stations. Stations may include one or more instruments for performing a specific task (e.g., a pipette is an instrument that may be used at an immunoassay station to interact with samples on an automation track). Except where noted otherwise, the concepts of module and station may be referred to interchangeably.

Tubes/sample vessels/fluid containers: Samples may be carried in vessels, such as test tubes or other suitable vessels, to allow carriers to transport samples without contaminating the carrier surfaces.

Exemplary Embodiments

Embodiments of the present invention include systems and methods that provide a more efficient lab automation system. Embodiments of the present invention provide a significant increase in the number of reagent types that can be used to perform tests from an available test menu without significantly increasing the overall size of the system. Embodiments of the present invention provide a significant increase in the percentage of tests that can be performed while maintaining the number of modules having testing stations and maintaining the number of local reagent storage areas proximate to each module and/or testing station by storing the less frequently used uncommon reagents at a central reagent storage area and the more frequently used common reagents at local reagent storage areas proximate to the testing stations. Embodiments of the present invention provide a more efficient lab automation system by determining the time and location that the less frequently used uncommon reagents are needed for testing and directing the less frequently used uncommon reagents from the central reagent storage area to the determined location at the determined time.

An exemplary track geometry, for use in transporting payloads, such as sample tubes within an analyzer typical in prior art configurations, is shown in FIG. 1. As used herein, an analyzer can refer to any automated system or preparing or testing properties of patient samples in an automated manner. This track can include prior art friction tracks, which may introduce problems in designing a track system. However, certain embodiments of the present invention could also use a similar geometry without necessarily employing a friction track for motion. Track 100 can be a generally oval-shaped track that conveys samples in pucks or trays between various stations, such as sample preparation analyzing/testing stations 110, 120, and 130. Track 100 could be a single direction track or, in some instances, a linear bidirectional track. In this exemplary set-up, each analyzer 110, 120, 130 is serviced by a respective sidecar 112, 122, 132. At the junction between the track 100 and each sidecar, a gate or switch can be placed that allows samples to be diverted to or from track 100 to the sidecar. The oval nature of track 100 can be used to circulate samples while they wait for access to each analyzer. For example, analyzer 110 may have a full queue in sidecar 112, such that new samples on track 100 cannot be diverted to sidecar 112 until analyzer 110 finishes handling a pending sample in sidecar 112 and inserts it back into the main traffic flow of track 100.

In some prior art systems, each sidecar can be serviced by a handling mechanism such as sample probe arms 114, 124, and 134. These robotic handling arms can aspirate sample material from samples in a sidecar via a probe needle, or can pick up a sample tube from the sidecar and transport it into the corresponding testing station. In this exemplary system, the available testing stations include an immunoassay station 110, a low-volume chemistry station 120, and an expandable dilution/ISE electrolyte and high-volume chemistry (station or stations) 130. Some advantages of this approach are that the track 100 can be part of a separate lab automation system that can be added onto otherwise self-contained stations, and the track 100 and stations 110, 120, and 130 can be independently upgraded, purchased, or serviced. Some stations, such as high-volume chemistry station 130, can include their own friction track 136 that operates independently of track 100. Friction track 136 can include a bidirectional friction track that allows samples to move between sub-modules of high-volume chemistry station 130. A drawback of this type of system is that the separate friction tracks operate independently and control of overall automation becomes more complicated. Furthermore, transitions between friction tracks 136 and 100 can be slow and cumbersome, particularly where there is no direct route between two friction tracks. In some systems, moving between tracks may require lifting and placing samples via a robot arm.

Prior art lab automation systems for analyzers generally treat individual analyzer/testing stations as generic destinations for a sample on the track. In some embodiments of the present invention, the lab automation system can be integrated within the individual testing stations, which can substantially reduce or eliminate the complexity of the individual testing stations and reduce the need for separate sample handling systems within each station. In some embodiments, by integrating the lab automation system into the stations, the system can begin to treat individual stations less as generic destinations and more as portions of a multi-route track onto which a sample can travel.

FIG. 2A shows one embodiment of a track system that can be adapted for use with the present invention. Track 150 is a rectangular/oval/circular track on which sample carriers move in a clockwise (or counterclockwise) direction. Track 150 may be unidirectional or bidirectional. Carriers can transport any suitable payload within an IVD environment, such as fluid samples, reagents, or waste. Fluids, such as patient samples, can be placed in a container or vessel, such as a test tube, vial, cuvette, etc. that can be transported by a carrier. Carrier, as used herein, is a general term for pucks, trays, or the like for handling material in accordance with the disclosed embodiments. Carriers, and, by extension, payloads such as samples, can move on the main track 150 or be diverted via decision points such as 164 or 166. These decision points can be mechanical gates (as in the prior art) or other mechanisms suitable for allowing a sample to be diverted from the main track 150 to a sidecar, such as 160, 160A, 160B, 160C as described herein. By way of example, if a sample carrier is traversing the main path 150 and reaches decision point 166, it can be made to continue on the main track to segment 162 or it can be made to divert to sidecar 160. The systems and methods by which the decision can be made to divert the sample carrier at decision point 166 are described throughout.

FIG. 2B shows an alternative track layout that may be suitable for certain embodiments of the present invention. Track 170 is also a generally circular track with sample carriers moving clockwise (or counterclockwise). In this example, rather than having sidecars outside of the track, pullouts 180, 180A, and 180B are chords within the track. Similarly, when sample carriers reach decision points, they may be diverted off of the main path to a side path such as path 180. At decision point 186, a sample on the main track 170 can be made to continue on the main track or be diverted onto path 180. Once an analyzer station along handling path 180 is done processing the sample, the sample proceeds to decision point 184 where it may be placed back onto the main path 170.

Figure 3:
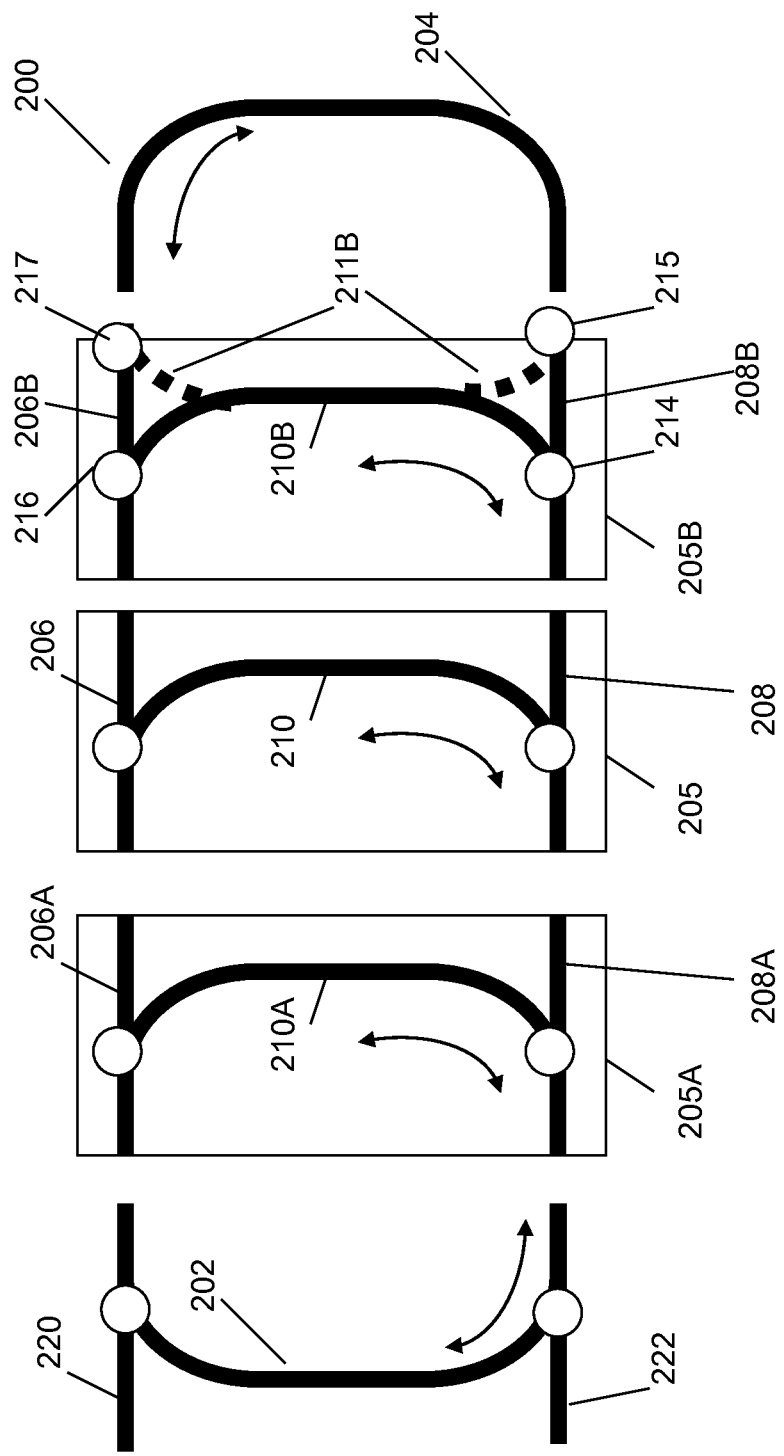
FIG. 3 is a diagrammatic view of an exemplary modular track configuration that can be used with the embodiments disclosed herein.

FIG. 3 shows a modular approach to the automation system track that can be used for certain embodiments of the present invention. In this example, the tracks may be integrated into individual analyzer stations, such that the track can be used as part of the internal motion or sample handling system of individual lab stations. In the prior art, it is common to have multiple different types of motion systems within different analyzer/testing stations. For example, some stations can include friction tracks for shuttling pucks or trays of sample tubes, and may include carousels containing smaller vessels, such as cuvettes and reaction vessels, into which portions of the sample can be aspirated and dispensed. In some embodiments, by integrating portions of the track system into the analyzer stations themselves, each station can include its own queuing logic and may be simplified to eliminate unnecessary internal motion systems.

With respect to FIG. 3, the track 200 can be broken into modular components that are integrated into analyzer modules. In this exemplary track, modules 205, 205A, and 205B can be combined with one another and optionally other modular track components 202 and 204 to form a track similar to that shown in FIG. 2B. For instance, 205A can be a module that performs the same function as immunoassay 110 (FIG. 1), 205 can be a module that performs the same function as low-volume chemistry module 120 (FIG. 1), and 205B can be a module that performs ISE electrolyte testing, like module 130 (FIG. 1). In this example, the main outer track can be formed by track segments 202, 204, 206, 206A, 206B, 208, 208A, and 208B. Within the analyzer modules 205, 205A, and 205B, internal paths 210, 210A, and 210B form pullouts from the main track. The internal paths can be used for internal queuing and can be managed independently within each analyzer module to allow each module to have greater control over samples to be processed.

One advantage of integrating track 200 and sub-paths 210, 210A, and 210B into the analyzer modules 205, 205A, and 205B, respectively, is that the internal handling mechanisms within each analyzer module can be specially adapted to better coordinate with the track sub-paths. In some embodiments, modules 205, 205A, and 205B can be adapted to process each sample within a period that is less than an operation cycle of the overall analyzer, leaving enough time for the sample to be routed along the track system to another module after processing, allowing the other module to immediately process the sample on the next operation cycle. As used herein, an operation cycle is a unit of time used by scheduling algorithms to allot processing time to modules for sample assays. These can be dynamic or fixed and can allow synchronous operation of the modules in the analyzer and provide a reliable timing model for scheduling samples amongst multiple modules in the analyzer. The operation cycle time can be chosen to be the time needed by any given module between when it starts processing a first sample, and when it is ready to process another sample under expected steady-state conditions. For example, if an analyzer can process one test every three seconds, and the expected average tests per sample is seven, the operation cycle time can be 21 seconds. It should be understood that individual modules can implement efficiency techniques, such as parallelism or processing multiple samples within a cycle, to maximize throughput, even when the number of tests-per-sample varies from an expected amount. Furthermore, it should be understood that in some embodiments, individual modules have different operation cycle times, and these modules can operate substantially asynchronously from one another. Virtual queues or buffers can be used to assist the management of sample scheduling where cycle times or demand vary between modules.

Enabling transit between modules in the analyzer in a reliable time frame, on the order of a single operation cycle or less, achieves many performance advantages not possible with prior art track systems. If a sample can be reliably handled by an analyzer module and transported to the next analyzer module within a single cycle of the analyzer, traffic handling in queuing becomes much simpler, throughput becomes more consistent, and latency can be controlled and reduced. Essentially, in such an analyzer, a sample can reliably be handled by the track system and processed uniformly such that a sample does not sit idly on the track system waiting in queues. Furthermore, queues within the system, such as queues within a given analyzer module, can reliably be shortened, limited by the number of modules within the system.

In some embodiments of the present invention, the reliable and rapid nature of the track system enables queues to be virtual, rather than physical. A virtual queue can be handled in software, rather than by physical limitations. Traditionally, queues have been physical. The simplest physical queue is effectively a traffic jam at any given part of a sample handling operation. A bottleneck creates a first-in first-out (FIFO) queue, where sample carriers are effectively stopped in a line, providing a buffer so that an analyzer or a decision point can request the next sample in the queue when it is ready. Most prior art lab automation tracks maintain FIFO processing queues to buffer samples that are waiting to be processed by the attached modules (analyzers or pre/post analytic devices). These buffers allow the track to process sample tubes at a constant rate, even though the modules or operator requests can create bursts of demand. FIFO queues can also substantially increase the throughput of the individual modules by allowing them to perform preprocessing tasks for future samples, for example, prepare a cuvette or aspirate reagent, while processing the current sample. While the rigid predictability of FIFO queues enables the parallelization of some processing tasks, it also can prevent the modules from using opportunistic scheduling that may increase throughput by reordering tests on samples to optimize resources. For example, the internal resource conflicts of most immunoassay analyzers can be so complex that the analyzers need to interleave the tests from multiple samples in order to reach maximum efficiency. A FIFO queue can reduce the throughput of these analyzers by as much as 20%. Another challenge with FIFO queues is their inability to handle priority samples (e.g., a STAT sample). If a STAT sample needs to be processed immediately, the entire FIFO queue has to be flushed back onto the main track, delaying all other samples on the track and forcing the original module to slowly rebuild its queue.

Another type of queue is a random access (RA) queue. A carousel is an example of a physical RA queue found in analyzer modules. By aliquoting a portion of a sample into one or more vessels in a carousel ring, an analyzer module can select any of a number of samples to process at any time within the analyzer. However, carousels have many drawbacks, including added complexity, size, and cost. A carousel also increases the steady-state processing time, because a sample must be transferred into and out of the random-access queue. Processing delays depend on the implementation, such as the number of positions in a carousel. On the other hand, by having random access to samples, a local scheduling mechanism within a module can process samples in parallel, performing sub-steps in any order it desires.

In some embodiments, carousels or other RA queues can be eliminated from the modules and the sub-paths (e.g., 210) from the automation system can be used as part of an RA or FIFO queue. That is, if the travel time for a sample between any two points can be bounded to a known time that is similar to that of a carousel (such as predictably less than a portion of an operation cycle), the track 200 can be part of the queue for a given module. For example, rather than using a carousel, module 205 can utilize samples in carriers on sub-path 210. Preprocessing steps, such as reagent preparation, can be conducted prior to the arrival of a sample under test. Once that sample under test arrives, one or more portions of the sample can be aspirated into cuvettes or other reaction vessels for an assay. In some embodiments, these reaction vessels can be contained within module 205, off track, while in other embodiments, these reaction vessels can be placed in carriers on sub-path 210 to allow easy motion. If the sample under test is required to be at a module for longer than an operation cycle, or if multiple samples will be processed by the module during an operation cycle, the sub-path 210 can act as a queue for the module.

Furthermore, samples not yet under test, which may be currently located at other modules, can be scheduled for the next operation cycle. These next-cycle samples can be considered as residing in a virtual queue for module 205. A module can schedule samples to arrive during a given operation cycle for any sample on track 200. A central controller, or controllers associated with modules themselves, can resolve any conflicts over a sample for a given cycle. By giving a module prior knowledge of the arrival time of a sample, each module can prepare resources and interleave tests or portions of tests to more efficiently allot internal resources. In this manner, modules can operate on samples in a just-in-time manner, rather than by using large physical buffers. The effect is that the virtual queue for a given module can be much larger than the physical capacity of the sub-path serving that module, and existing scheduling algorithms can be used. Effectively, each module can treat track 200 as it would treat a sample carousel in a prior art module.

It should be appreciated that by employing virtual queues, in some embodiments, multiple modules can have multiple queues and can share a single queue or samples within a queue. For example, if two modules are equipped to perform a certain assay, a sample needing that assay can be assigned to a virtual queue for that assay, which is shared between the two modules capable of handling the assay. This allows load balancing between modules and can facilitate parallelism. In embodiments where reaction vessels are placed in carriers on track 200, an assay can be started at one module (e.g., reagents prepared and/or sample mixed in) and the assay can be completed at another (e.g., a reaction is observed at another module). Multiple modules can effectively be thought of as a multi-core processor for handling samples in some embodiments. In these embodiments, scheduling algorithms for the multiple modules should be coordinated to avoid conflicts for samples during a given operation cycle.

By employing virtual queues, modules can operate on samples while the samples are in the virtual queues of other modules. This allows low latency of samples, as each sample that is placed onto track 200 can be processed as quickly as the modules can complete the tests, without having to wait through a physical queue. This can greatly reduce the number of sample carriers on track 200 at any given time, allowing reliable throughput. By allowing modules to share queues or samples, load balancing can also be used to maximize throughput of the system.

Another advantage of using virtual queues is that STAT samples can be dynamically assigned priority. For example, a STAT sample can be moved to the head of any queue for the next operation cycle in software, rather than having to use a physical bypass to leapfrog a STAT sample to the head of a largely static physical queue. For example, if a module is expecting three samples to be delivered by track 200 for assays during the next operation cycle, a scheduler responsible for assigning samples to the module can simply replace one or more of the samples with the STAT sample, and have the track 200 deliver the STAT sample for processing during the next operation cycle.

If decision points such as 214 and 216 can be streamlined such that there is no need for a queue at each decision point, the only physical queues can be within sub-paths 210, 210A, and 210B. As described above, these can be treated as RA queues or FIFO queues. If a STAT sample is placed onto track 200, RA queues within sub-paths 210, 210A, and 210B need not be flushed, as the STAT sample can be processed immediately. Any FIFO queues can be individually flushed. For example, if a STAT sample is placed onto track 200 at section 222, the sample may be routed to the appropriate analyzer 205B via the outside track and decision point 216. If there are other samples (and by extension the sample carriers transporting those samples) waiting in the queue in path 210B, only those samples in the queue may need to be flushed to allow a STAT sample to take priority. If the outer track 200 is presumed to take less than an operation cycle to traverse, any samples that were flushed from the queue in 210B can simply be circulated around the track and placed immediately back into the queue in path 210B immediately behind the STAT sample, eliminating any down time caused by the STAT sample.

Entry paths 220 and 222 can be used to input samples to the track 200. For example, regular priority samples can be placed onto track 200 at input 220 and STAT priority samples can be placed on input 222. These inputs can be used as outputs for samples when complete, or other ports (not shown) can be used as the output paths for used samples. Input 220 can be implemented as an input buffer, acting as a FIFO queue for input samples seeking access to the track 200. Once a sample reaches the head of the queue at input 220, it can be moved onto the track (either by being placed in a carrier, or by being placed in a carrier when it is placed in input 220). A STAT sample can enter the track 200 immediately after being placed at input 222 or, if track 200 is overcrowded, the STAT sample can enter the track at the next available uncrowded operation cycle. Some embodiments monitor the number of carriers on the track during an operation cycle and limit the total number to a manageable amount, leaving the remainder in input queues. By restricting samples at the input, track 200 can be free of traffic, allowing it to always be operated in the most efficient manner possible. In these embodiments, the transit time of a sample between two modules can be a bounded value (e.g., less than some portion of an operation cycle), allowing simplified scheduling.

In some embodiments, the track system 200 can be designed to be bidirectional. This means that sample carriers can traverse the outside path and/or any sub-paths in either direction. In some embodiments, additional sub-paths, such as 211B accessed via additional decision points 215 and 217, can assist in providing bidirectional access. Bidirectional paths can have inherent advantages. For example, if normal priority samples are always handled in the same direction, a STAT sample can be handled in the opposite direction along the sub-path. This means that a STAT sample can essentially enter the exit of the sub-path and be immediately placed at the head of the queue without requiring the queue to be flushed. For example, if a STAT sample is placed on track 200 at segment 204, it can enter path 210B via decision point 214 and proceed into path 210B to be immediately placed at the head of any queue. Meanwhile, in all of these examples, because queues are presumed to be limited generally to sub-paths, there is no need to flush queues in other modules if a STAT sample does not need immediate access to those modules. Any additional modules that need to service a STAT sample on a subsequent cycle can flush their queues at that point, providing just-in-time access to a STAT sample without otherwise disrupting the operation of each analyzer module.

Modular design also allows certain other advantages. If the automation systems within an analyzer module are adapted to take advantage of the track system contained in the module, new features can be added that use the common track. For example, a module could have its own internal reagent carousel that includes all of the reagents necessary for performing the assays prescribed for the samples. When reagents stocked in the analyzer module run low, an operator can replenish the reagents in some embodiments by simply loading additional reagents onto carriers on the track 200. When the reagents on track 200 reach the appropriate module, the module can utilize mechanical systems such as an arm or a feeder system that takes the reagents off of the track and places the reagents in the reagents store for the module.

In some embodiments, the individual track portions shown in FIG. 3 and FIG. 2A and FIG. 2B can be operated independently from one another, or can be passive. Independent carrier movement provides advantages over friction-based track systems, such as non-localized conveyor belts where the entire friction track must be moved to effect movement of a sample carrier. This means that other samples also on that track must move at the same rate. This also means that if certain sections operate at different speeds, collisions between passive carriers carrying samples can occur.

FIG. 4A depicts an exemplary carrier 250 for use with the present invention. Carrier 250 can hold different payloads in different embodiments. One payload can be a sample tube 255, which contains a fluid sample 256, such as blood or urine. Other payloads may include racks of tubes or reagent cartridges, or any other suitable cartridge. Sample carrier 250 includes a main body 260, which can house the internal electronic components described herein. The main body 260 supports a bracket 262, which can accept a payload. In some embodiments, such as a sample tube, this is a shallow hole (slot) that is designed to accept a fluid container 255, such as a sample tube, and hold it with a friction fit. In some embodiments, the friction fit can be made using an elastic bore or a clamp that can be fixed or energized with a spring to create a holding force. In some embodiments, sample racks and reagent cartridges can be designed to also attach to the bracket 262, allowing bracket 262 to act as a universal base for multiple payload types.

Body 260 can include or be coupled to guide portion 266, which allows the carrier 250 to follow a track between decision points. Guide portion 266 can include, for example, a slot to accept one or more rails in the track, providing lateral and/or vertical support. In some embodiments, the guide portion allows the carrier 250 to be guided by walls in the track, such as the walls of a trough-shaped track. The guide portion 266 can also include drive mechanisms, such as friction wheels that allow a motor in the carrier body 260 to drive the carrier or puck 250 forward or backward on the track. The guide portion 266 can include other drive components suitable for use with the embodiments described throughout, such as magnets or induction coils.

Rewritable display 268 can be provided on the top of the carrier 250. This display can include an LCD oriented panel and can be updated in real time by the carrier 250 to display status information about sample 256. By providing the electronically rewritable display on the top of the carrier 250, the status information can be viewed at a glance by an operator. This can allow an operator to quickly determine which sample he/she is looking for when there are multiple carriers 250 in a group. By placing the rewritable display on top of the carrier 250, an operator can determine status information even when multiple carriers 250 are in a drawer or rack.

Figure 4B:
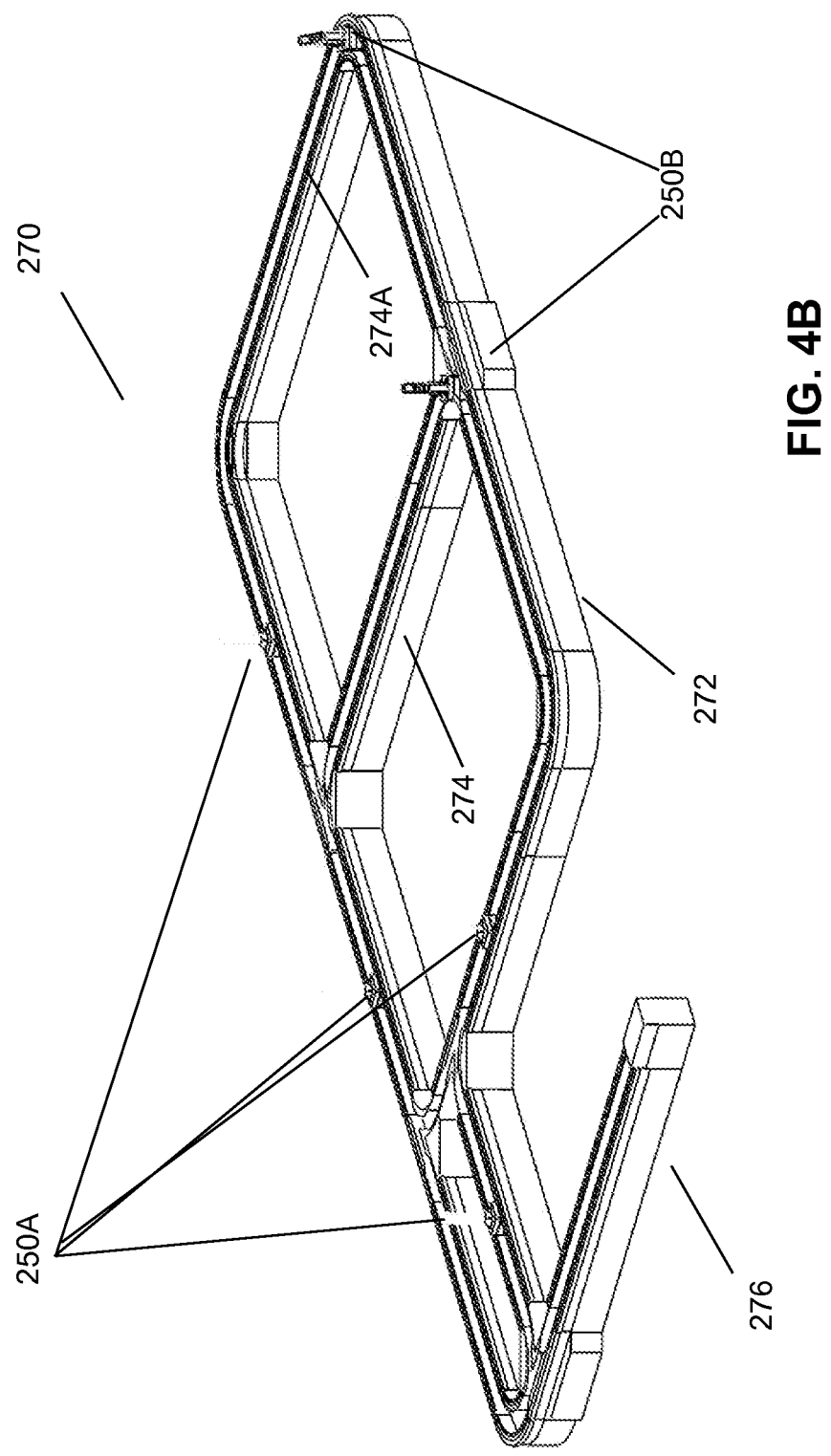
FIG. 4B is a perspective view of an exemplary track configuration that can be used with the embodiments disclosed herein.

FIG. 4B shows an exemplary track configuration 270 for use by carriers 250. In this example, carriers 250A transport sample tubes, while carriers 250B transport racks of tubes along main track 272 and/or subpaths 274 and 274A. Path 276 can be used by an operator to place samples into carriers or remove samples from these carriers.

Figure 4C:
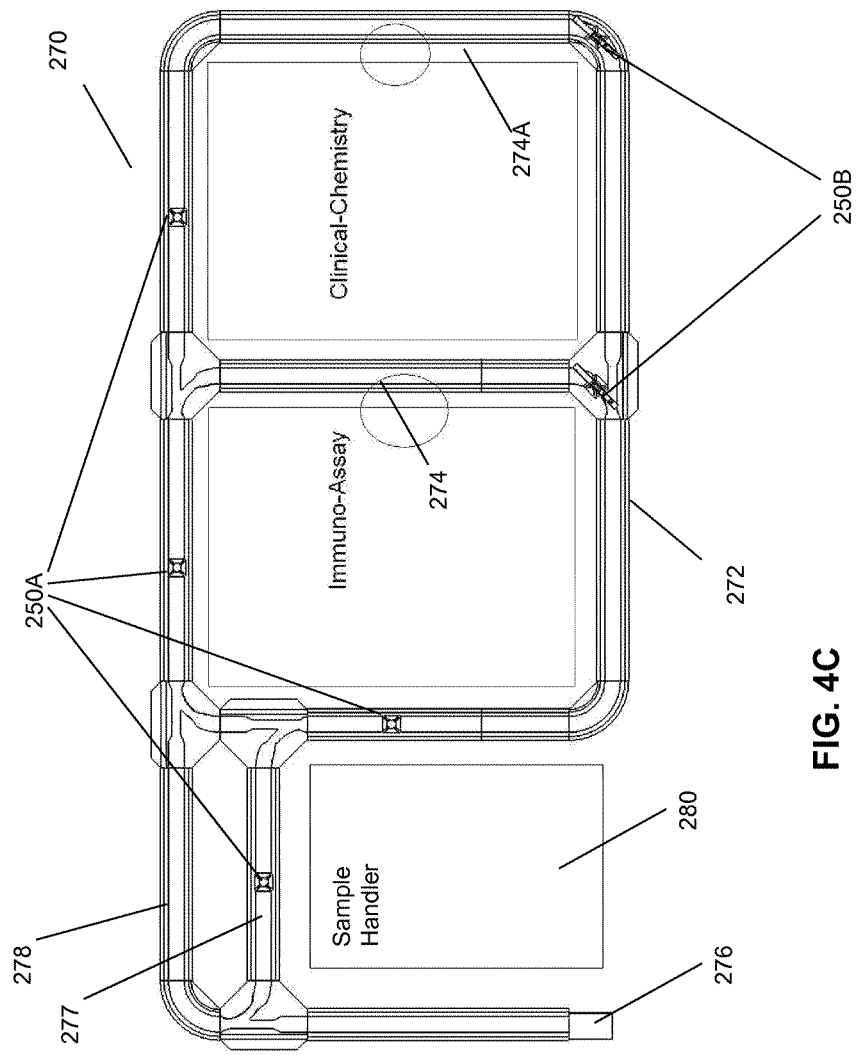
FIG. 4C is a top view of an exemplary automation system that can be used with the embodiments disclosed herein.

FIG. 4C shows an additional view of an exemplary track configuration 270. In this example, sub-path 274 serves an immunoassay station, while sub-path 274A serves a clinical chemistry station. Input/output lane 276 can be served by a sample handler station 280 that uses sub-paths 277 and 278 to buffer samples for insertion or removal of the samples from the main track 272.

In some embodiments, the sample handler 280 can also load and unload samples or other payloads to/from the carriers 250A and 250B. This allows the number of carriers to be reduced to the amount needed to support payloads that are currently being used by the stations in track system 270, rather than having a vast majority of carriers sitting idle on tracks 277 and 278 during peak demand for the analyzer. Instead, sample trays (without the carriers disclosed herein) can be placed/removed by an operator at input/output lane 276. This can reduce the overall cost of the system and the number of carriers needed can be determined by the throughput of the analyzer, rather than based on anticipating the peak demand for the analyzer in excess of throughput.

Intelligent Carriers

Whereas some embodiments may utilize passive pucks or trays (e.g., the puck is a simple plastic or rubber brick that lacks active or autonomous systems, power, onboard processing, or control) to reduce cost and complexity, in some embodiments the added complexity and cost necessary to integrate intelligence and autonomy into individual carriers (which can include smart pucks or trays in some embodiments) can provide certain benefits. Accordingly, embodiments of the present invention can utilize intelligent carriers to enable certain improvements over passive pucks on the friction-based tracks. For example, one disadvantage of prior art track systems is that, at each decision point, the decision for directing a puck is made by the track by rotating the puck and reading a barcode optically. Rotating and optical reading is a relatively slow process. Furthermore, this process can be redundant because the system has a prior knowledge of the identification of the sample tube when the sample tube is placed into the puck by an operator. Embodiments of the present invention can include carriers that have means to identify the contents of the sample tube (and optionally communicate this information to the automation system) without requiring the carrier to be stopped, rotated, and read optically.

For example, a carrier can include an onboard optical reader to automatically read a barcode of a payload. The results of the scan can then be stored in the memory of a carrier if the carrier has onboard processing capability. Alternatively, an outside source, such as a hand barcode reader operated by an operator at the time of placing the sample into the carrier, can communicate the barcode information of the payload to the carrier via RF signal or other known means, such as communication protocol using temporary electrical contact or optical communication. In some embodiments, the association of the carrier with the payload can be stored external to the carrier and the identity of the carrier can be conveyed by the carrier to the system by RF, optical, or near-field communication, allowing the system to assist in routing or tracking the carrier and the payload. Routing decisions can then be made by the carrier or by identifying the carrier, rather than reading a unique barcode of a payload.

By moving processing capability and/or sensor capability onto each individual carrier, the carriers can participate actively and intelligently in their own routing through the track system. For example, if individual carriers can move independently of one another either by autonomous motive capabilities or by communication with the track, certain performance advantages can be realized.

By allowing carriers to move independently, carriers can move around the track faster. One key limitation on the motion of a carrier is that it should not spill an open-tube sample. The limiting factor is generally not the velocity of the carrier in a straight line, but the acceleration and jerk experienced by the carrier (while speeding up, slowing down, or turning), which may cause splashing. For prior art friction-based track systems, the velocity of the track is typically limited to prevent acceleration and jerk experienced by pucks from exceeding threshold amounts because the entire track moves. However, by using a track system with independently operating sections that can respond to individual carriers, or individual carriers that have independent motive capability, the acceleration of any given carrier can be tailored to limit acceleration/deceleration and jerk, while allowing the average velocity to be greater than that of traditional tracks. By not limiting the top speed of a carrier, the carrier can continue to accelerate on each track section as appropriate, resulting in a substantially higher average speed around the track. This can assist the carrier in traversing the entire track system in less than one machine cycle of the analyzer. These machine cycles can be, for instance 20 or 40 seconds.

Similarly, an autonomous carrier can know its own identity and that of its payload. This allows the carrier to actively participate or assist in the routing decision process at individual decision points. For example, upon reaching a decision point (e.g., switch, intersection, junction, fork, etc.), a carrier can communicate its identity and/or the identity of its payload to the track or any switching mechanism (or its intended route that the carrier has determined based on the payload identity), via RF or near-field communication. In this scenario, the carrier does not need to be stopped at a decision point for a barcode scan. Instead, the carrier can keep going, possibly without even slowing down, and the carrier can be routed in real time. Furthermore, if the carrier knows where it is going or communicates its identity to the track (such that the track knows where the carrier is going) before the carrier physically reaches a decision point, the carrier can be made to decelerate prior to a decision point if the carrier will be turning. On the other hand, if the carrier does not need to turn at the decision point, the carrier can continue at a higher velocity because the sample carried by the carrier will not undergo cornering forces if the carrier is not turning at the decision point or a curved section of the track.

An autonomous carrier can also include onboard processing and sensor capabilities. This can allow a carrier to determine where it is on the track and where it needs to go, rather than being directed by the track (although, in some embodiments, a central controller sends routing instructions to the carrier to be carried out). For example, position encoding or markers in the track can be read by a carrier to determine the carrier's location. Absolute position information can be encoded on a track surface to provide reference points to a carrier as it traverses the track. This position encoding can take many forms. The track may be encoded with optical markers that indicate the current section of the track (e.g., like virtual highway signs), or may further include optical encoding of the specific absolute location within that section of track (e.g., like virtual mile markers). Position information can also be encoded with markings between absolute position marks. These can provide synchronization information to assist a carrier in reckoning its current trajectory. The optical encoding scheme may take on any appropriate form known to one skilled in the art. These marks used by the encoding scheme may include binary position encoding, like that found in a rotary encoder, optical landmarks, such as LEDs placed in the track at certain positions, barcodes, QR codes, data matrices, reflective landmarks, or the like. General position information can also be conveyed to the carrier via RF/wireless means. For example, RFID markers in the track can provide near field communication to the carrier to alert the carrier that it has entered a given part of the track. In some embodiments, local transmitters around or near the track can provide GPS-like positioning information to enable the carrier to determine its location. Alternatively, sensors in the track, such as Hall effect sensors or cameras, can determine the position of individual carriers and relay this information to the carrier.

Similarly, the carrier can have sensors that indicate relative motion, which provide data that can be accumulated to determine a position between absolute position marks. For example, the carrier may have gyroscopes, accelerometers, or optical sensors that observe speckle patterns as the carrier moves to determine velocity or acceleration, which can be used to extrapolate a relative position. In some embodiments, components include a light source and an image sensor that can be used to observe the relative motion of the track surface with respect to the carrier to determine a real-time trajectory estimate. For example, after reckoning its position with an absolute position mark, the carrier can observe successive images of a track surface and compare these images to determine the direction and magnitude of motion. This can be used to determine real-time position, velocity, acceleration, and jerk, or estimates thereof. In addition, synchronous marks, such as marks placed at regular intervals in the track, can be used to reckon the carrier's position between absolute position marks and can correct errors that may have accumulated in the real-time trajectory information determined from observation of the relative motion of the surface of the track. This can allow a lower sampling frequency or less precise components in the position decoding imaging sensor.

Because a carrier can know where it is and its motion relative to the track, a carrier can essentially drive itself, provided it knows its destination. The routing of the carrier can be provided in many different ways in various embodiments. In some embodiments, when a carrier is loaded with the sample, the system can tell the carrier the destination analyzer station. This information can be as simple as the identification of the destination station in embodiments where the carrier has autonomous routing capability. This information can also be detailed information such as a routing list that identifies the specific path of the individual track sections and decision points that a carrier will traverse. Routing information can be conveyed to the carrier via any communication method described herein, such as RF communication, near-field/inductive communication, electrical contact communication, or optical communication.

In an exemplary embodiment, when an operator scans the barcode of the sample tube and places it in a carrier, the system determines the identity of the carrier and matches it with the identity of the sample. The system then locates the record for the sample to determine which tests the sample must undergo in the analyzer. A scheduler then allocates testing resources to the sample, including choosing which tests will be done by individual testing stations and when the sample should arrive at each testing station for analysis. The system can then communicate this schedule (or part of the schedule) to the carrier to inform the carrier of where it needs to go, and optionally when it needs to go and/or when it needs to arrive.

Once the carrier is placed onto the track system, the routing capabilities and location acquisition systems of the carrier enable the carrier to determine where it is on the track and where it needs to go on the track. As the carrier traverses the track, the carrier reaches individual decision points and can be directed along the main track or along sub-paths as appropriate. Because each carrier operates independently from one another, a carrier can do this quite quickly without necessarily stopping at each decision point and without waiting for other carriers in a queue. Because these carriers move quickly, there is less traffic on the main sections of the track, which reduces the risk of collision or traffic jams at decision points or corners in the track (e.g., sections where carriers might slow down to avoid excessive forces on the sample).

Motive force can be provided to the carriers in many ways. In some embodiments, the track actively participates in providing individualized motive force to each carrier. In some embodiments, motive force is provided by electromagnetic coils in the track that propel one or more magnets in the carrier. An exemplary system for providing this motive force is the track system provided by MagneMotion, Inc., which can generally be understood by the description of the linear synchronous motors (LSMs) found in US Published Patent Application 2010/0236445, assigned to MagneMotion, Inc. These traditional systems utilizing this magnetic motion system have included passive carriers that lack the integrated intelligence of the carriers described herein, and all routing and decisions are made by a central controller with no need for active carriers that participate in the routing and identification process.

In embodiments that utilize magnetic motion, the electromagnetic coils and the magnets operate as an LSM to propel each individual carrier in the direction chosen with precise control of velocity, acceleration, and jerk. Where each coil on the track (or a local set of coils) can be operated independently, this allows highly localized motive force to individual carriers such that individual carriers can move with their own individually tailored accelerations and velocities. Coils local to a carrier at any given moment can be activated to provide precise control of the direction, velocity, acceleration, and jerk of an individual carrier that passes in the vicinity of the coils.

In some embodiments, a track may be comprised of many individually articulable rollers that act as a locally customizable friction track. Because individual micro-sections of the track can be managed independently, rollers immediately around a carrier may be controlled to provide individualized velocity, acceleration, and jerk. In some embodiments, other active track configurations can be used that provide localized individual motive force to each carrier.

In some embodiments, the track may be largely passive, providing a floor, walls, rails, or any other appropriate limitations on the motion of a carrier to guide the carrier along a single dimension. In these embodiments, the motive force is provided by the carrier itself. In some embodiments, each individual carrier has one or more onboard motors that drive wheels to provide self-propelled friction-based motive force between the track and the carrier. Unlike traditional friction tracks, where the track is a conveyor, carriers with driven wheels can traverse the track independently and accelerate/decelerate individually. This allows each carrier to control its velocity, acceleration, and jerk at any given moment to control the forces exerted on its payload, as well as traverse the track along individually tailored routes. In some embodiments, permanent magnets may be provided in the track and electromagnets in the carrier may be operated to propel the carrier forward, thereby acting as an LSM with the carrier providing the driving magnetic force. Other passive track configurations are also contemplated, such as a fluid track that allows carriers to float and move autonomously via water jets or the like, a low friction track that allows carriers to float on pockets of air provided by the track, (e.g., acting like a localized air hockey table), or any other configuration that allows individual carriers to experience individualized motive forces as they traverse the track.

Figure 5:
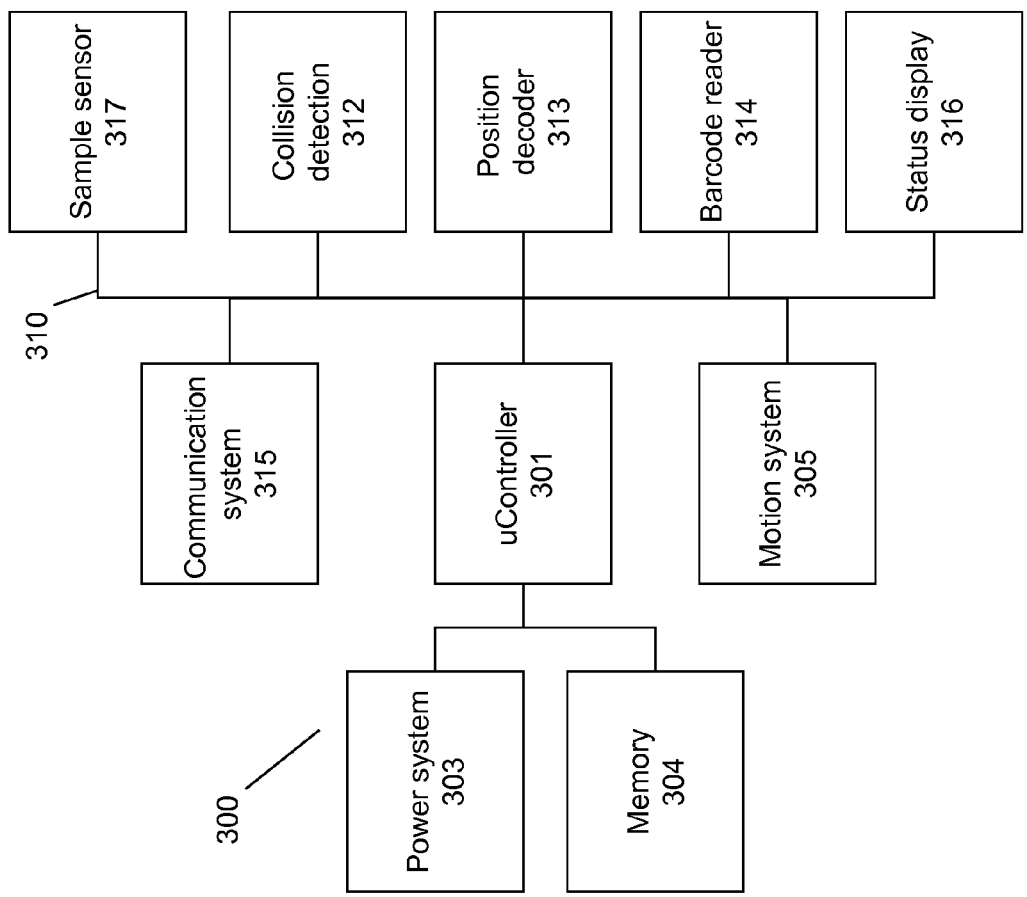
FIG. 5 is a system block diagram of the control systems including onboard active carriers that can be used with certain embodiments disclosed herein.

FIG. 5 shows a top-level system diagram of the control systems and sensors for an exemplary intelligent autonomous carrier 300. Carrier 300 can be any suitable embodiment of a carrier, such as a carrier 250, shown at FIG. 4A, that is configured to hold a single fluid container 255. Carrier 300 is controlled by an onboard processor, such as microcontroller 301 that includes sufficient processing power to handle navigation, maintenance, motion, and sensor activities needed to operate the carrier. Because the carrier is active and includes onboard electronics, unlike prior art passive carriers, the carrier includes an onboard power station. The details of this station vary in different embodiments of the present invention. In some embodiments, power system 303 comprises a battery that may be charged as the carrier operates, while, in other embodiments, the battery is replaceable or can be manually charged when the carrier is not operating. Power system 303 can include the necessary charging electronics to maintain a battery. In other embodiments, the power system 303 comprises a capacitor that may be charged by inductive or electrical contact mechanisms to obtain electrical potential from the track itself, in much the same way a subway car or model train might receive power.

Microcontroller 301 communicates with system memory 304. System memory 304 may include data and instruction memory. Instruction memory in memory 304 includes sufficient programs, applications, or instructions to operate the carrier. This may include navigation procedures as well as sensor handling applications. Data memory in memory 304 can include data about the current position, speed, acceleration, payload contents, navigational plan, identity of the carrier or payload, or other status information. By including onboard memory in carrier 300, the carrier can keep track of its current status and uses information to intelligently route around the track or convey status information to the track or other carriers.

Microcontroller 301 is responsible for operating the motion system 305, sensors 312, 313, and 314, communication system 315, status display 316, and sample sensor 317. These peripherals can be operated by the microcontroller 301 via a bus 310. Bus 310 can be any standard bus, such as a CAN bus, that is capable of communicating with the plurality of peripherals, or can include individual signal paths to individual peripherals. Peripherals can utilize their own power sources or the common power system 303.

Motion system 305 can include the control logic necessary for operating any of the motion systems described herein. For example, motion system 305 can include motor controllers in embodiments that use driven wheels. In other embodiments, motion system 305 can include the necessary logic to communicate with any active track systems necessary to provide a motive force to the carrier 300. In these embodiments, motion system 305 may be a software component executed by microcontroller 301 and utilizing communication system 315 to communicate with the track. Devices such as motors, actuators, electromagnets, and the like, that are controlled by motion system 305 can be powered by power system 303 in embodiments where these devices are onboard the carrier. External power sources can also provide power in some embodiments, such as embodiments where an LSM provides motive force by energizing coils in the track. In some embodiments, motion system 305 controls devices on or off the carrier to provide motive force. In some embodiments, the motion system 305 works with other controllers, such as controllers in the track, to coordinate motive forces, such as by requesting nearby coils in the track be energized or requesting the movement of local rollers. In these embodiments, motion system 305 can work together with communication system 315 to move the carrier.

Carrier 300 can include one or more sensors. In some embodiments, carrier 300 includes a collision detection system 312. Collision detection system 312 can include sensors at the front or back of a carrier for determining if it is getting close to another carrier. Exemplary collision detection sensors can include IR range-finding, magnetic sensors, microwave sensors, or optical detectors. Whereas many prior art pucks are round, carrier 300 may be directional, having a front portion and a rear portion. By having a directional geometry, carrier 300 can include a front collision detector and a rear collision detector.

In some embodiments, collision detection information can include information received via the communication system 315. For example, in some embodiments, the central controller for the track can observe the location and speed of carriers on the track and evaluate collision conditions and send updated directions to a carrier to prevent a collision. In some embodiments, nearby carriers can communicate their positions in a peer-to-peer manner. This allows carriers to individually assess the risk of collision based on real-time position information received from other carriers. It will be understood that in embodiments where the carrier receives trajectory information about other carriers, or decisions are made with the help of a centralized controller that has access to trajectory information of nearby carriers, the carriers need not be directional, and can include sensors or receivers that do not depend on a given orientation of a carrier.

Carrier 300 can also include a position decoder 313. This sensor can extrapolate the carrier's position as described herein. For example, position decoder 313 can include a camera or other optical means to identify landmarks in the track, or observe optical encoding in the track. In some embodiments, position decoder 313 can also include inertial sensors, magnetic sensors, or other sensors sufficient to determine a carrier's current position, direction, velocity, acceleration, and/or jerk.

Carrier 300 can optionally include a barcode reader 314. If equipped with barcode reader 314, carrier 300 can observe the barcode of its payload at the time the samples are loaded onto the carrier or at any time thereafter. This prevents the need for a carrier to stop at individual decision points to have the system read the barcode of a sample tube. By reading and storing the identity of the sample tube, or conveying this information to the overall system, a carrier may more efficiently traverse the track system because routing decisions can be made in advance of reaching a decision point. Alternatively, where a system knows the identity of the sample when it is placed onto the carrier, the system can include an external barcode reader and can convey the identity of the payload to the carrier for storage and memory 304 via communication system 315.

Communication system 315 can comprise any mechanisms sufficient to allow the carrier to communicate with the overall automation system. For example, this can include an XBee communication system for wireless communication using an off-the-shelf communication protocol, such as 802.15.4, any appropriate version of 802.11, or any standard or proprietary wireless protocol. Communication system 315 can include a transceiver and antenna and logic for operating an RF communication protocol. In some embodiments, communication system 315 can also include near-field communication, optical communication or electrical contact components. Information conveyed via the communications system to/from carrier 300 is described throughout this application.

In some embodiments, the carrier can also include a status display module 316. The status display module 316 can include a controller and rewritable electronic display, such as an LCD panel or E-ink display. In some embodiments, the controller is treated as an addressable portion of memory, such that the microcontroller 301 can easily update the status display 316.

In some embodiments, the carrier also includes sample sensor 317. This sensor can be used to indicate the presence or absence of a fluid container in the carrier's tube bracket (which may also be referred to as a tube holder). In some embodiments, this is a momentary mechanical switch that is depressed by the presence of a tube and not depressed when a tube is absent. This information can be used to determine the status of a tube, which can assist in the display of status information by status display module 316.

Routing

The desire for rapid transit times within an analyzer system can make routing difficult. In prior art systems, rapid routing is less critical because samples are generally stopped, singulated, and scanned at each decision point. In those systems, the routing decision for a given decision point can be made while the sample is stopped. Rapid routing decisions are generally desired, and may require determining a switching decision before a sample carrier reaches a decision point. Furthermore, because the carriers move at a rapid rate compared to the prior art, the control of the instantaneous trajectory of a sample carrier can be assisted by real-time processing in order to prevent spilling or damaging IVD samples. In some embodiments, substantially instantaneous trajectory observation and control is conducted onboard each carrier to facilitate real-time control, while the overall routing decisions are made by a central controller that manages a group of carriers. Therefore, in some embodiments of the present invention, the carriers act like semi-autonomous robots that receive global routing instructions from a central controller, but make local motion decisions substantially autonomously.

For example, when a carrier receives a sample (e.g., a patient fluid sample or other payload) a central controller managing one or more carriers determines the schedule for that carrier and instructs the carrier where to go on the track of, for example, an in vitro diagnostics automation system. This instruction can be a next-hop instruction (e.g., identifying the next leg of a route), such as going to a given decision point, moving forward to the next decision point, or turning at a given decision point. In some embodiments, the instructions can include a complete or partial list of track segments and decision points to be traversed and whether to turn at each decision point. These instructions can be communicated to the carrier from a central controller via any conventional means, including wireless or contact electrical signaling, as explained throughout this disclosure.

While following the instructions, each carrier can make a determination of the appropriate velocity, acceleration, and jerk (as used herein, acceleration includes deceleration). This can include a real-time decision of whether the carrier must slow down to avoid collision or to enter a curve without causing excessive lateral forces, or slow down before the next decision point. These decisions can be made with the assistance of any onboard sensors, as well as external information received by the carrier, such as information about the position and trajectory of nearby carriers. For example, accelerometers and/or track encoding information can be used to determine the current velocity, acceleration, and jerk, as well as the current position of a carrier. This information can be used by each carrier to determine its trajectory and/or can be conveyed to other carriers. Collision detectors, such as RF rangefinders, can determine whether or not a potential collision condition exists to assist the carrier in determining whether it needs to slow down and/or stop. This collision determination can include trajectory information about the current carrier, as well as the trajectory information about surrounding carriers received by the current carrier through observation or by receiving information from a central scheduler for the track.

Figure 6:
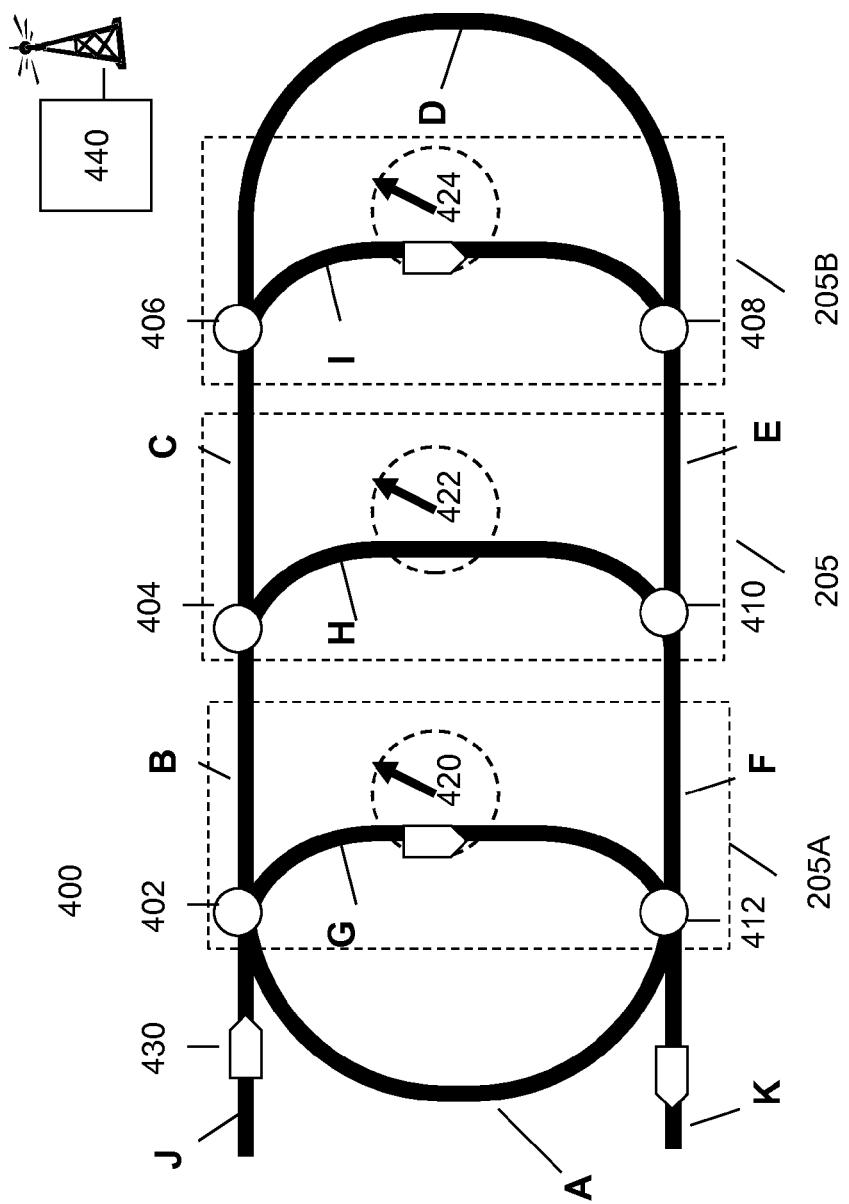
FIG. 6 is a diagrammatic view of exemplary routes in an exemplary track configuration that can be used for navigation of sample carriers in certain embodiments.

FIG. 6 shows an exemplary routing scenario in automation track system 400. Carrier 430 receives routing instructions from central management processor 440 via RF signaling. Central management processor 440 can participate in monitoring and directing carriers, including issuing routing instructions and scheduling the movement and dispatch of carriers. Central management processor 440 can be part of the central controller and/or local controllers that interact with individual modules or stations. Central or local controllers can also act at the direction of central management processor 440. Central management processor 440 can include one or more processors operating together, independently, and/or in communication with one another. Central management processor 440 can be a microprocessor, software operating on one or more processors, or other conventional computer means suitable for calculating the schedule for multiple carriers within the track system 400.

Central management processor 440 can receive position information from multiple carriers, as well as any sensor information from sensors in the track system 400 and/or information reported by the carriers. Carrier 430 can be any suitable embodiment of a carrier, such as carrier 300, shown in FIG. 5. Central management processor 440 uses the status information of the carriers and track as well as the identity of samples or other payload carried by the carriers and the required assays to be performed by the system on these samples.

The exemplary track 400 shown in FIG. 6 includes a first curve segment A, that connects to straight segment B and a pullout segment G, (e.g., a segment that serves a testing station), which serves analyzer/testing station 205A and pipette 420, via decision point 402. Segment B connects to straight segment C and a pullout segment H, which serves analyzer/testing station 205 and pipette 422, via decision point 404. Segment C connects to curved segment D, which serves sample handling station 205C, and pullout segment I, which serves analyzer/testing station 205B and pipette 424, via decision point 406. Segment D connects to straight segment E and the other end of pullout segment I, via decision point 408. That is, there are different paths between decision points 406 and 408—segments D and I (where segment I is a pullout that can be used to deliver samples to interact with pipette 424). Segment E connects to straight segment F and the other end of pullout segment H, via decision point 410. Segment F connects to curved segment A and the other end of pullout segment G, via decision point 412. In some embodiments, track 400 includes input and output lanes J and K, which can be used to add or remove carriers at decision points 402 and 412.

In some embodiments, decision points 402-412 are passive forks in the track that carrier 430 can navigate to select a proper destination segment. In other embodiments, decision points 402-412 are active forks that can be controlled by carrier 430 or central management processor 440. In some embodiments, decision points 402-412 are electromagnetically controlled switches that respond to requests by carrier 430, such as via RF or near-field communication. In some embodiments these electromagnetically controlled switches have a default position, such as straight, that the switch will return to once a carrier has been routed. By using default positions for decision points, a carrier may not need to request a position at each decision point, unless it needs to be switched at that decision point.

Scheduler central management processor 440 assigns carrier 430 a first route, Route 1, to place the carrier 430 and its payload within reach of pipette 420. Carrier 430 is instructed to travel along segment J to decision point 402 and travel onto segment G to stop at a position accessible to pipette 420. In some embodiments, carrier 430 receives the instructions and determines its current location and trajectory to determine a direction and trajectory to use to reach decision point 402. Carrier 430 can also take into account that it will be making a hard right turn at decision point 402 onto segment G. In some embodiments, decision point 402 includes a switching mechanism in the track that can operate under the control of carrier 430. In these embodiments, carrier 430 communicates with the track on approach to decision point 402 to request switching onto segment G. In other embodiments, carrier 430 may have a steering mechanism (such as moveable guide wheel, directional magnets, asymmetric brakes, or the like) that allows carrier 430 to make a right turn onto segment G at decision point 402, without the assistance of an external gate integrated into the track. In these embodiments, carrier 430 engages the steering mechanism at decision point 402 to make the turn onto segment G.

This determination can be based on observing the position encoding in the track, including consulting the onboard memory of the last known position. Near-field communication from the track can also be used to provide an identification of the current track and encoding scheme being used by the track. Carrier 430 can take into account that it will be making a hard right turn at decision point 402 onto segment G. Using position encoding, carrier 430 can determine where it is in relation to decision point 402 on track J and adjust this trajectory accordingly, to ensure that it approaches the decision point with appropriate velocity.

Carrier 430 can determine its rough location—its current track section, such as section J, by reading encoding in the track, such as optical encoding, or RFID tags. In some embodiments, carrier 430 uses multiple means to determine its location within the track system 400. For example, RFID tags can be used to determine generally on which track segment the carrier 430 is located, while optical encoding or other precise encoding can be used to determine the position within that track segment. This encoding can also be used to determine velocity, acceleration, or jerk by observing changes in the encoding (e.g., derivatives from the position information).

Carrier 430 can use the identification of the current track section to determine the appropriate route to the destination section either by explicit instruction received by the central management processor 440 or by looking up an appropriate route in an onboard database in memory 304, as shown in the onboard control systems in FIG. 5. In some embodiments, the carrier 430 has an understanding of how to reach section G from section J based on a map stored in the memory of carrier 430 in memory 304. This map can include a simple lookup table or a tree of track sections where each node is linked by the corresponding decision points, or vice versa. For example, upon identifying that the carrier is currently in the track section J, the onboard database can inform carrier 430 to proceed to decision point 402 to be switched to the right onto section G.

As shown in FIG. 6, carrier 430 responds to instructions for Route 1 by proceeding onto section G and stopping at a position near pipette 420. Once the carrier 430 is stopped, it can receive additional instructions from the analyzer/testing station controlling pipette 420. For example, analyzer 205A can control pipette 420 and can instruct carriers on section G to position themselves at precise points along section G. This allows analyzer/testing stations to treat track sections as random access queues. For example, once carrier 430 stops on section G, additional instructions can be conveyed via central management processor 440 or directly from analyzer 205A to the carrier 430 via RF transmission or other means, such as local optical or inductive/near-field signals. These instructions can include halting while another carrier interacts with pipette 420, and subsequently proceeding to a position accessible to pipette 420, when analyzer 205A is ready to perform one or more assays on the sample carried by carrier 430.

Once analyzer/testing station 205A has finished interacting with the sample carried by carrier 430, additional routing instructions can be sent to the carrier 430 from the central management processor 440. For example, Route 2 can include routing instructions to proceed to section H to interact with pipette 422. In some embodiments, the routing tables contained within onboard memory 304 of carrier 430 have sufficient information about the track layout to allow the carrier to route itself to section H. In other embodiments, a list of routing steps can be transmitted to carrier 430 via central management processor 440. It will be appreciated that other embodiments can include conveying any subset of the route to carrier 430 and/or sending routing instructions in a piecemeal fashion, such that carrier 430 always knows the next routing step, and optionally subsequent routing steps.

In this example, carrier 430 receives a route list representing Route 2 from central management processor 440 instructing it to proceed via section G to decision point 412. At decision point 412, carrier 430 will initiate switching onto section A by interacting with a gate or by turning as described above. Carrier 430 can take into account curved track conditions on section G and section A to ensure that acceleration and jerk conditions do not exceed a threshold requirement for the sample it carries. This can prevent spillage or instability during transit. The route information received by carrier 430 then instructs carrier 430 to proceed through decision point 402 without turning. The trajectory used in Route 2 when approaching decision point 402 can be different (e.g., faster) from that used during Route 1, because carrier 430 knows that it does not need to make a sharp right turn onto section G. In some embodiments, this allows carrier 430 to approach decision point 402 with a substantially greater velocity during Route 2 than during Route 1. By traversing decision point 402 faster if carrier 430 is not turning, carrier 430 can complete Route 2 in less time than embodiments in which carrier 430 must slow down for possible switching at each decision point. This is an improvement over the prior art, where carriers are typically halted and singulated, regardless of whether the carrier is turning or not.

After passing decision point 402, carrier 430 proceeds onto section B. At decision point 404, carrier 430 proceeds to section C. At decision point 406, carrier 430 prepares and turns onto section I, where it stops for interaction with pipette 424. Like section G, section I can act as a queue for pipette 424 and carrier 430 can be controlled under local instruction by the analyzer/testing station 205B served by section I.

When pipette 424 is done interacting with carrier 430, central management processor 440 can provide new routing instructions to carrier 430 instructing carrier 430 to proceed onto an output path K. Route 3 can be handled in the same manner as Route 1 and Route 2. Upon receiving instructions for Route 3, carrier 430 proceeds down section I to decision point 408 where it turns back onto a main track section E and proceeds past decision point 410, track section F, and decision point 412 (without needing to slow down in some embodiments), and onto section K where the carrier 430 and/or the sample can be removed from the system by an operator. Carrier 430 can then be reused for samples at input section J.

Test Menu Expansion System

While carriers have thus far been often described with respect to transporting samples, it should be understood that carriers are not limited to those that transport samples (e.g., sample carriers). For example, the same mechanisms described with respect to transporting samples may also be used to transport, along the track, a variety of types of reagent delivery carriers (e.g., reagent wedges) that include one or more reagents for performing the tests.

As described above, IVD reagent manufacturers typically offer a test menu that includes a large number of possible tests. Each test in an available test menu may include one or more types of reagents to combine with a sample. Conventional automation systems may, however, perform only a small subset of tests available from the possible test menu because of the limited reagent storage capacity at each module and/or station. Because most conventional automation systems may not store the full test menu of reagents on their analyzers, labs may send out some of the samples to other (specialty) labs, thereby incurring lost opportunity and loss of potential income.

Due to the limited reagent storage capacity, conventional systems typically store more of the common reagents used in the more frequently performed tests (commodity tests) than the uncommon reagents used in the less frequently performed tests (esoteric tests). The esoteric tests may, however, provide a higher profit margin than the commodity tests. Therefore, a lab that outsources esoteric tests to meet the demand for commodity tests may experience a loss of potential income.

Typically, laboratories have their own test menus that include tests that are selected from a larger reagent manufacturer test menu. FIG. 7 is a table illustrating percentages of laboratories' test menus used by different sized (number of tests per day) laboratoriess to perform different percentage of each laboratory's respective tests. For example, as shown at the table in FIG. 7, a small lab (performing 4,757 tests per day) uses 22% of the test menu to perform 85% of their 4,757 tests per day. The data illustrated in the table at FIG. 7 shows that a small percentage of reagent test types (ranging from 14% to 39%) accounted for a large majority of reagent tests run (85% to 95%) for all of the different sized labs. That is, the conventional systems used only 14% to 39% of the available reagent test menu to perform 85% to 95% of their daily tests.

In order to perform a larger percentage of reagent tests using the conventional systems, the overall size of the systems would need to be enlarged to store and transport the increased number of reagent types used at each analyzer. For example, the enlarged overall size of a system may include an increased number of analyzers, modules, and/or storage areas at each module. The enlarged overall size may include also include larger sized reagent storage areas and larger tracks (e.g., increasing the width of the track or the number of lanes along the track), resulting in a more complex and costly system.

Embodiments of the present invention include systems that increase the percentage of tests performed from the test menu without increasing the number or size of reagent storage areas at each module and/or testing station and without enlarging the size of the tracks by storing the less frequently used uncommon reagents at a central reagent storage area, determining the time and location that the less frequently used uncommon reagents are needed for testing and directing the less frequently used uncommon reagents from the central storage area to the determined location at the determined time. In some embodiments, the determined time may be a point in time (1:00 p.m. today, 3:00 p.m. on Tuesday, immediately following completion of another test). In other embodiments, the determined time may be any interval of time (e.g. 5 minute interval, 1 hour interval, between 1:00 and 1:15, on Monday, within 10 minutes following the completion of another test).

Figure 8:
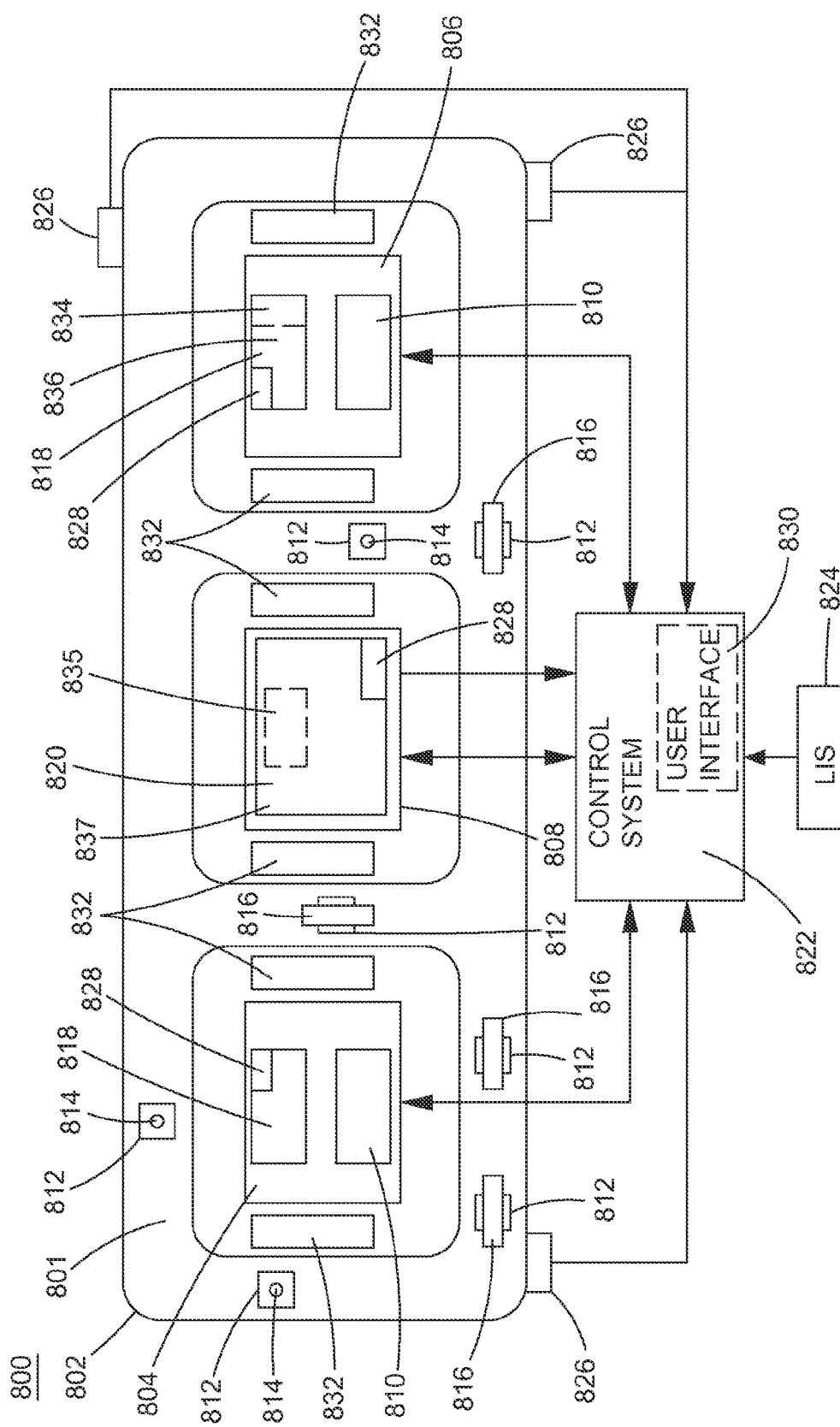
FIG. 8 is a schematic diagram illustrating a system that includes an analyzer having a track and plurality of modules that can be used with the embodiments disclosed herein.

FIG. 8 is a schematic diagram illustrating a system 800 that includes an analyzer 802 having a track 801 and plurality of modules 804, 806 and 808. As described above, a module 804, 806 may include a station, such as testing stations 810. Embodiments may include more than one station and may also include different types of stations. In some embodiments, an automation system may include analyzers having any number of modules and any number of stations. The geometry of analyzer 802 illustrated at FIG. 8 is merely exemplary. Other embodiments may include an analyzer having any type of geometry.

As shown at FIG. 8, carriers 812 may hold a sample tube containing a sample fluid. Carriers 812 may also hold a reagent carrier 816 (e.g. reagent wedge) which may contain different types of reagents. Embodiments may include carriers that hold one or more sample tubes and one or more reagents. Embodiments may also include carriers that are configured to hold both reagents and samples. Testing stations 810 may be configured to perform one or more tests by combining one or more reagents in reagent wedges 816 with one or more samples in sample tubes 814.

The analyzer 802 shown at FIG. 8 also includes local storage areas 818 at the modules 804 and 806 and proximate to testing stations 810. In some embodiments, local storage areas may be located at testing stations and, in some aspects, may be integral with testing stations. Each of the local storage areas 818 may be configured to store one or more common reagents used in the more frequently performed tests. The analyzer 802 also includes a central reagent storage area 820 configured to store one or more uncommon reagents used in the less frequently performed tests. In some embodiments, analyzers may include more than one central storage area. By storing the less frequently used uncommon reagents at the central reagent storage area 820 (e.g., not environmentally controlled) instead of the local reagent storage areas 818, the size of each of the larger quantity of local reagent storage areas 818 may be reduced (thereby reducing the overall size of the system) while maintaining the same amount of reagents needed to perform a high percentage of the available test menu.

In some aspects, however, common reagents may also be stored in central storage areas and uncommon reagents may be stored in the local storage area if the reagent usage and reagent timing warrants it. In some aspects, common reagents and/or uncommon reagents may also be directed to locations (e.g., storage areas and testing stations) from locations on the track 801.

As shown at FIG. 8, analyzer 802 also includes control system 822. Control system 822 may be used to: (i) direct the less frequently used uncommon reagents from the central storage area 820 to one or more locations (e.g., analyzers 802, testing stations 810, module 804, 806, and 808) at a time (e.g., scheduled times, predicted times, and/or immediately) or within a time interval, and (ii) direct the common reagents from the local storage areas 818 to the locations to perform the less frequently performed tests at the time or within the time interval.

In some embodiments, scheduling information may be used to determine times and locations. For example, control system 822 may be configured to determine the time and location that the less frequently used uncommon reagents are needed for testing and direct the less frequently used uncommon reagents from the central reagent storage area 820 to the testing stations 810 at the determined time based on received scheduling information. Control system 822 may also be configured to determine the time and location that the more frequently used common reagents are needed for testing and direct the common reagents from the local storage areas 818 to the testing stations 810 to perform the more frequently performed tests based on the received scheduling information. Control system 822 may also direct the uncommon reagents and/or the common reagents are directed to the testing stations directly from the track 801.

The scheduling information may include information indicating an amount of the one or more reagent types scheduled to be combined with the one or more samples at one or more scheduled times. The scheduling information may also include information indicating an amount of the one or more reagent types scheduled to be combined with the one or more samples at the one or more testing stations. In some embodiments, an amount of the one or more reagent types may refer to the number of tests of each type that will be used. In some embodiments, an amount of the one or more reagent types may refer to the actual volume of reagent that will be used.

In some aspects, the scheduling information may include scheduling information received via a scheduling information storage device, such as a laboratory information system (LIS) 824. The LIS 824 may include test orders requiring one or more reagents at specific times (e.g., 1:00 on Tuesday) or over a specific period of time (e.g., on Tuesday or next week). Control system 822 may analyze the test orders entered into the LIS, and determine the test menu required for a specific time or time period. The LIS 824 may also include known schedules for amounts of each type of reagent needed at predetermined testing stations 810. For example, the LIS 824 may include one or more specific amounts of one or more corresponding specific reagents for a test to be performed at testing station 810 at module 804 at 1:00 p.m. on Tuesday. The LIS 824 may also include one or more specific amounts of one or more corresponding specific reagents for a test to be performed at testing station 810 at module 806 at 2:00 p.m. on Tuesday. The LIS 824 may include information corresponding to any number of tests over any predetermined time period (e.g., hour, day, week, month).

In some aspects, the scheduling information may be received via a user interface 830 configured to receive scheduling information from an operator. The user interface 830 may include a touch-sensitive input component that is integrated with a display, such as a capacitive, resistive or other type of touch screen. Alternatively, the touch-sensitive component may be an item of hardware that is separate from the display, such as a touch pad or trackpad, a keyboard and a mouse. The control system 822 may also receive inputs from other remote devices (not shown). For example, the user interface 830 may be configured to scheduling information that includes test menu requirements for different points in the day, such as testing required for samples to be received at 1:00 pm from a hospital's oncology ward and samples to be received at 5:00 pm from the hospital's cardiac ward. Control system 822 may predict the test menu required based on the received scheduling information via the user interface 830.

In some aspects, the control system 822 may direct common reagents and uncommon reagents based on historical testing information. Control system 822 may analyze historical test order information for test menu patterns (e.g., a number of oncology related samples appearing frequently at 1:00 pm and/or a number of cardiac related samples appear at 5:00 pm every day). Control system 822 may predict the test menu required based on the analyzed historical test order information. Historical testing information may include one or more previous times that a reagent type has been tested. Historical testing information may also include test order information indicating one or more previous times that a reagent type has arrived at the system for testing.

Control system 822 may also be in communication with various components of system 800. For example, as shown at FIG. 8, control system 822 may be in communication with each module 804, 806 and 808. Control system 822 may also be in communication with the local storage areas 810, central storage area 820, and pick and place devices 832 at each module. In some aspects, control system 822 may also be in direct communication with local storage areas 810, central storage area 820, and pick and place devices 832 at each module 804, 806 and 808. In other aspects, control system 822 may also be in communication with local storage areas 810, central storage area 820, and pick and place devices 832 via local or sub controllers (not shown).

In some embodiments, the control system 822 may not be in communication with the LIS 824 or any other system. That is, the control system 822 may not receive testing information from the LIS 824. For example, control system 822 may receive requests for reagents directly from system components including: (i) one or more analyzers, such as analyzer 802 shown at FIG. 8 and analyzers 1002 and 1004 shown at FIG. 10, (ii) one or more modules, such as modules 804, 806 shown at FIG. 8 and module 1008 shown at FIG. 10 and/or (iii) one or more testing stations 810.

In some embodiments, the control system 822 may direct one or more of the plurality of reagents based on information indicating which testing station is configured to perform the one or more tests. For example, some testing stations may be configured to perform only a percentage of tests from the available test menu. The controller 822 may receive information indicating which of the testing stations are configured to perform certain tests and, based on the testing station information, may direct one or more of the plurality of reagents to a testing station determined to be able to perform a scheduled test.

As shown at FIG. 8, the system 800 may include various sensors, such as storage area sensors 828, which may sense the amounts and types of reagents stored at the local storage areas 810 and central storage area 820. System 800 may include track sensors 826, which may sense the amounts, types and location of reagents on the track 801. Control system 822 may receive the reagent information from the storage area sensors 828 and track sensors 826 indicating the amounts, types and location of reagents. In some embodiments, control system 822 may receive the reagent information from the carriers 812 indicating the location of the reagents via their own location on the track as well as the amounts and/or types and of reagents being carried. The reagent information may indicate an amount of each type of common reagent stored at the local storage areas 828, an amount of each type of uncommon reagent stored at the central storage area 820, locations of each type of common reagent on the track 801, and locations of each type of uncommon reagent on the track 801.

Based on any of the received information, the control system 822 may direct reagents to and from various locations, such as local storage areas 818, central reagent storage area 820, testing stations 810 and portions of the track 801. For example, based on information (e.g., scheduling information, historical information, reagent storage and location information) received, the control system 822 may direct one or more common reagents from a local reagent storage area 818 to a testing station 810 proximate to the local reagent storage area 818 to perform one or more of the frequently performed tests.

In some embodiments, control system 822 may direct one or more common reagents from a local reagent storage area 818 to central reagent storage area 820. For example, based on received information, control system 822 may determine that one or more common reagents may not be needed within a predetermined time in the near future and, in response to the determination, may direct the one or more common reagents to the central reagent storage area 820 to free up more space for reagents that are needed within a predetermined amount of time in the near future. The control system 822 may then direct the one or more common reagents in the central reagent storage area 820 to one or more testing stations 818 at a determined time based on the received information.

According to an aspect of some embodiments, the local storage areas 818 may include at least one short term storage area 836 if the control system 832 determines that the reagents are to be used for testing in the near future. In some embodiments, the local storage areas 818 may also include a long term storage area (e.g. chamber) 834 which controls environmental conditions (e.g., temperature and humidity), thereby preserving the reagents in storage for an amount of time (e.g., one or more days) if the control system 832 determines that the reagents are not to be used for testing in the near future. For example, control system 822 may direct reagents from central storage area 820 to the long term storage area 834 and/or may direct reagents from the short term storage area 836 of local storage area 818 to the long term storage area 834 if the control system 832 determines that the reagents are not to be used for testing in the near future.

Based on received scheduling information and/or storage information, control system 822 may direct the reagents from the long term storage area 834 directly to the one or more testing stations 818 at a determined point in time or within a determined time interval. Control system 822 may also direct the reagents from the long term storage area 834 to short term storage area 836 before being directed to the one or more testing stations 818. In some embodiments, the reagents may be initially stored in the local storage areas 818 by an operator. As shown at FIG. 8, central storage area 820 may also include a long term central storage area 835 a short term central storage area 837. Accordingly, control system 822 may determine uncommon reagents that are not needed in the near future be directed to the long term central storage area 835 and determine uncommon reagents that are needed in the near future be directed to the short term central storage area 837.

In some embodiments, the controller may be configured to indicate a need and/or a time for reagents to be transferred between short term storage areas (e.g., short term local storage areas 836 and short term central storage 837) and long term storage areas (e.g., long term local storage areas 834 and long term central storage 835) and indicate (e.g., display) the need and/or a time for the reagents to be transferred. In response, an operator may manually transfer reagents between the short term storage areas 836 and 837 and long term storage areas 834 and 835.

According to some embodiments, groups of reagents may be stored in packs. Each pack may include a group of common reagents of a particular type or a group of uncommon reagents of a particular type. As described above, because conventional systems typically store multiple packs of common reagent types, the amount of available space for storing a variety of types of reagents is decreased, thereby further reducing the number of tests that may be run from the available test menu.

Control system 822 may direct packs of reagents, such as one or more uncommon reagent type packs, from central reagent storage area 820 to the one or more of the testing stations 818 to perform one or more tests based on the received scheduling information. In some embodiments, control system 822 may direct the reagent type packs having at least one reagent remaining in the respective reagent type packs back to central reagent storage area 820 after the one or more tests is performed or to the one or more local reagent storage areas after the one or more tests is performed based on received information.

Figure 9B:
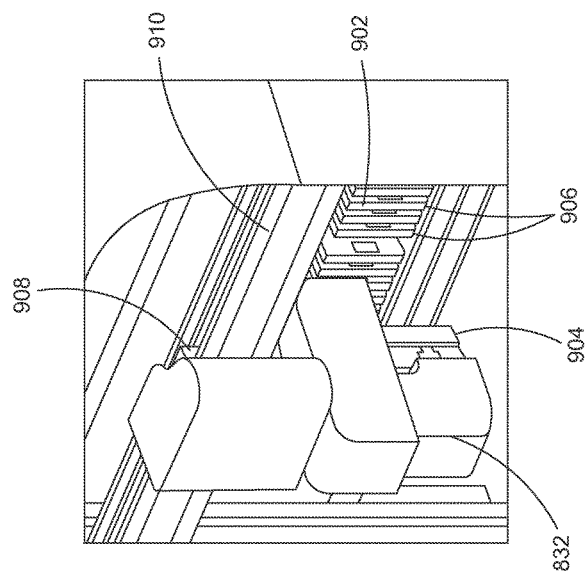
FIG. 9B is a perspective view of an exemplary pick and place device holding a reagent pack and adjacent to a reagent drawer of a central reagent storage area that can be used with the embodiments disclosed herein.
Figure 9A:
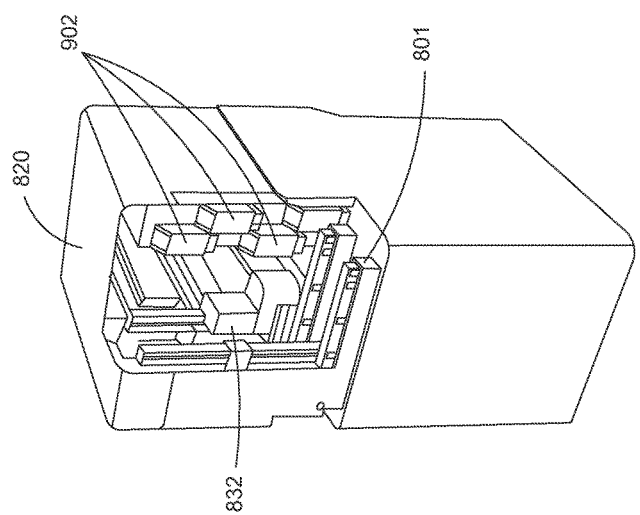
FIG. 9A is a perspective view of a central reagent storage area having storage drawers for storing reagents that can be used with the embodiments disclosed herein.

The control system 822 may direct packs of reagents and reagents within the packs of reagents to and from the various locations using pick and place devices 832. The location and quantity of pick and place devices 832 shown at the embodiment in FIG. 8 are merely exemplary. Embodiments may include any number of pick and place devices to move reagents to and from the various locations. FIG. 9A is a perspective view of central reagent storage area 820 which may include storage drawers 902. As shown at FIG. 9A, exemplary pick and place device 832 may be located proximate to central reagent storage area 820 and a portion of track 801. As shown at FIG. 9B, exemplary pick and place device 832 may be used to transport reagent packs 906 to and from a reagent drawer 902. As shown at FIG. 9B, exemplary pick and place device 832 may include a slidable portion 908 which may be configured to slide along a bar 910. Embodiments of the invention may include any place and pick device configured to pick up objects, such as packs of reagents and reagents within the packs of reagents, move the objects to and from different areas and place the objects at other areas. Pick and place devices may include robotic arms having one or more movable joints capable of moving in one or more dimensions, slidable portions moving in one or more dimensions, and a variety of types of actuation devices for moving one or more portions of the pick and place devices, such as linear actuators, pneumatic actuators, hydraulic actuators and electro-mechanical actuators.

By storing the reagents until they are needed for testing, determining times and locations for testing and directing the reagents to the determined locations at the determined times, a larger variety of reagents may be used for testing without having to enlarge the track to hold reagents until they are needed on the track and without having to provide more local storage space to hold the reagents until they are needed.

Because different tests from the test menu typically react at different levels based on the concentration of the reagent material, reagents must either be monitored for recalibration or must be continually recalibrated at periodic intervals. For example, each lot of each reagent type may be calibrated once to compensate for lot-to-lot variation in reagent manufacturing. Controls need to be run much more frequently, however, to accurately measure amounts of analyte in a specimen with a known concentration to generate accurate results. By utilizing control system 822 and the received information, such as the scheduling information and storage information, the system 800 may also direct that the stored common and uncommon reagents be calibrated at a predetermined time prior to their scheduled testing, eliminating the need to continually recalibrate the reagents until they are scheduled for testing and providing additional cost saving to the system 800. Further, if testing times for less frequently performed test are provided by the scheduling information far enough in advance, then controls and/or calibrators for the less frequently performed tests may be run at a predetermined time before (e.g. shortly before) the reagents for the less frequently performed tests are used, increasing analyzer throughput and reducing cost.

Control system 822 may also may also determine other information, such as lot-to-lot variations in the composition of reagents and control analyzers to perform testing based on the lot-to-lot variations. Confirm Control system 822 may also communicate with calibration systems and control other operations of an analyzer, such as determining whether analyzer's produce correct answers for specimens with known concentrations.

In some embodiments, control system 822 may control one or more mechanisms, such as a mechanical device (not shown) that pushes empty packs off of the track and into a trash bin to dispose of empty reagent packs. In some embodiments, control system 822 may direct empty packs to be moved from one or more local reagent storage areas 818 to one or more central reagent storage areas 820. Removing the empty reagent packs from the local reagent storage areas 818 may provide more space to store other reagent packs at the local reagent storage areas 818 and provide operators with a more efficient system of disposing of empty packs, thereby improving operator workflow.

Control system 822 may include central management processor 440. Carriers, such as carrier 812, which may hold one or more reagents and/or one or more samples, may receive routing instructions from central management processor 440. Control system 822 may participate in monitoring and directing carriers, including issuing routing instructions and scheduling the movement and dispatch of carriers. Control system 822 may be part of the central controller and/or local controllers that interact with individual modules 804, 806 and 808 and/or stations 810. Central or local controllers can also act at the direction of control system 822. Control system 822 may include one or more processors operating together, independently, and/or in communication with one another. Control system 822 may include a microprocessor, software operating on one or more processors and a medium including instructions for causing the one or more processors to direct the one or more common reagent types and the one or more uncommon reagent types to different locations based on received scheduling information. Control system 822 may also be in communication with the LIS 824, any of the modules 804, 806 and 808 and/or stations 810, track sensors 826, storage area sensors 828, one or more carriers 812 and one or more remote devices (not shown) that may send information to control system 822.

The embodiment shown at FIG. 8 shows a single track 801 which may be used to transport carriers holding reagents and carriers holding samples. In some embodiments, an automation system may include a reagent track to transport reagent carriers between storage areas and testing areas and a separate sample track to transport sample carriers between storage areas and testing areas. The control system may direct the one or more samples along the sample track and direct the plurality of reagents along the reagent track.

Figure 10:
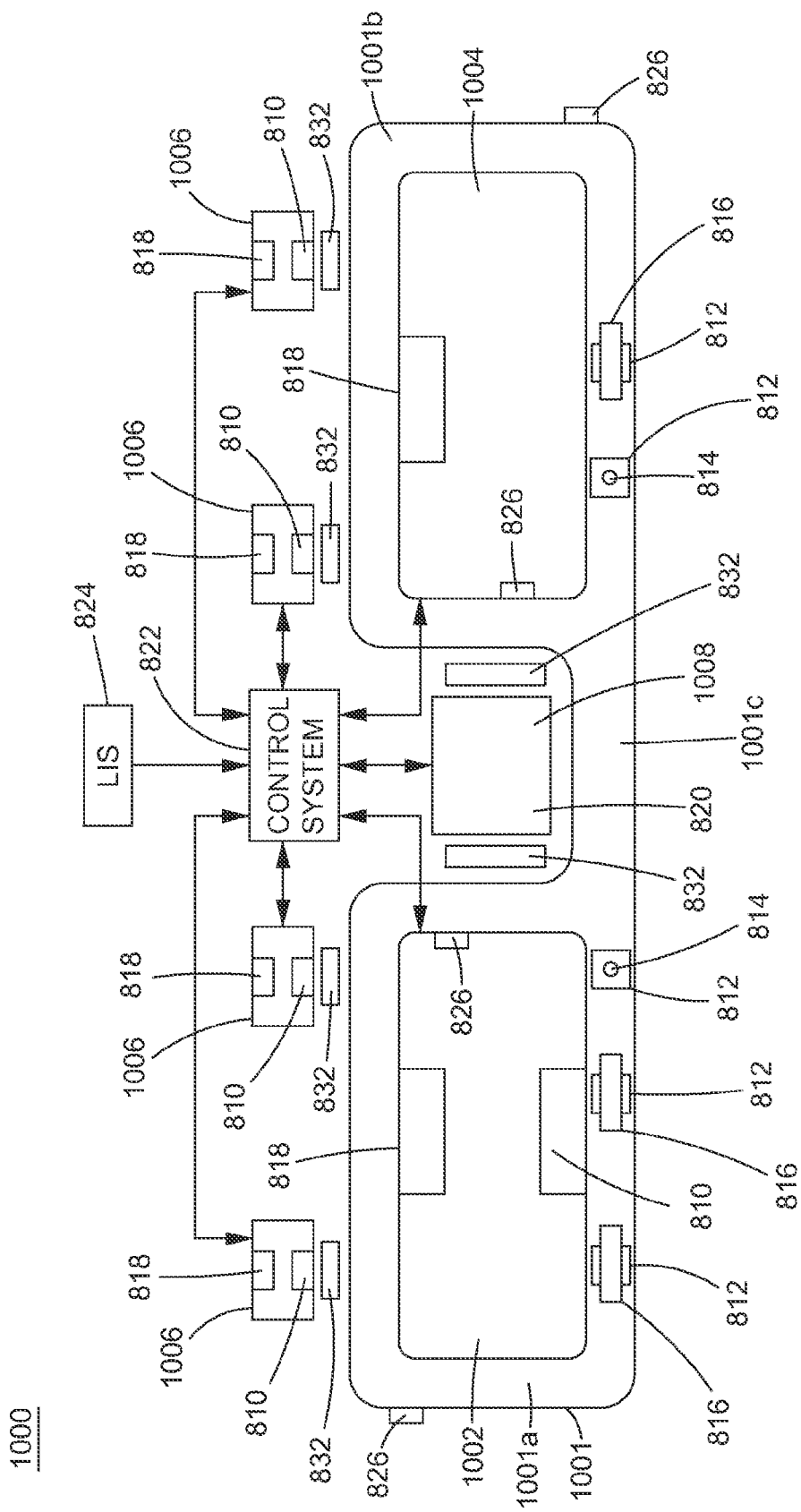
FIG. 10 is a schematic diagram illustrating a plurality of analyzers each having a plurality of modules that can be used with the embodiments disclosed herein.

In some embodiments, an automation system 1000 may also include a plurality of analyzers 1002 and 1004. FIG. 10 is a schematic diagram illustrating a plurality of analyzers 1002 and 1004 each including a plurality of modules 1006. Each of the analyzers 1002 and 1004 may include any one or more of the components of analyzer 802 shown at FIG. 8. For example, each of the modules 1006 may include or one or more stations, such as testing stations 818 shown at FIG. 8 and may also include one or more local reagent storage areas 818 located at or proximate to the one or more testing stations 810 and configured to store one or more common reagents of the plurality of reagents. The system 1000 may also include a central module 1008 that includes central reagent storage area 820. Central reagent storage area 820 may be configured to store one or more uncommon reagents of the plurality of reagents. Embodiments may include automation systems having analyzers with any number of modules and any number of stations.

In the embodiment shown at FIG. 10, first analyzer 1002 includes a first track portion 1001a of track 1001 and second analyzer 1004 includes a second track portion 1001b of track 1001. Track portions 1001a and 1001b are connected by connecting track portion 1001c. In some embodiments, track portions of corresponding analyzers may not be connected to each other. Further, the geometry of system 1000 illustrated at FIG. 10 is merely exemplary. Other embodiments may include automation systems having various geometries. Further, the geometry of one analyzer may be the same as or different from the geometry of another analyzer.

As shown at FIG. 10, the system 1000 may also include a control system 822 configured to direct the one or more common reagents from the one or more local reagent storage areas 818 of each respective analyzer 1002 and 1004 to the one or more testing stations 810 of each respective analyzer 1002 and 1004 to perform the one or more tests based on the received scheduling information described above with reference to FIG. 8. Control system 822 may also be configured to direct the one or more uncommon reagents from the central reagent storage area 820 of module 1008 to the one or more testing stations 810 of each respective analyzer 1002 and 1004 to perform the one or more tests based on the received scheduling information.

Figure 11:
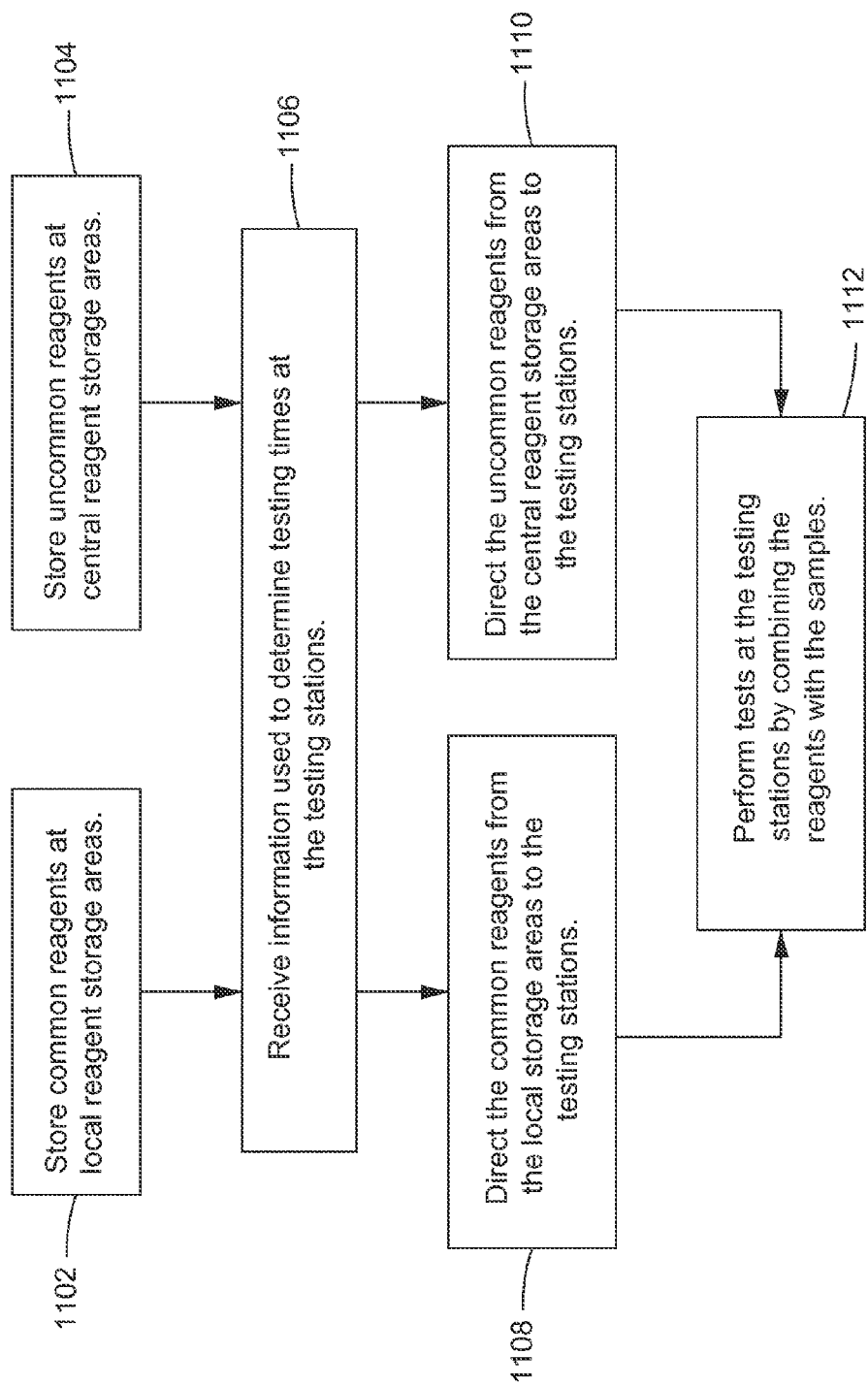
FIG. 11 is a flow diagram illustrating a method for operating an in vitro diagnostics system that can be used with the embodiments disclosed herein.

FIG. 11 is a flow diagram illustrating a method for operating an in vitro diagnostics system that can be used with the embodiments disclosed herein. As shown at block 1102, the method may include storing one or more common reagents at one or more local reagent storage areas. For example, common reagents to be used in the more frequently performed tests may be stored at one or more local reagent storage areas 818 located at or proximate to one or more testing stations 810. As shown at block 1104, the method may also include storing one or more uncommon reagents at one or more central reagent storage areas. For example, uncommon reagents to be used in the less frequently performed tests may be stored at central reagent storage area 820.

As shown at block 1106, the method may also include receiving information used to determine at least one testing time at the one or more testing stations 810 for one or more of the plurality of reagents to be combined with one or more samples. The received information used to determine at least one testing time may include scheduling information, historical testing information, reagent location information, reagent storage information and testing station information. For example, control system 822 may receive scheduling information indicating one or more reagent types scheduled to be combined with the one or more samples at the at least one scheduled testing time. Control system 822 may also receive scheduling information indicating an amount of the one or more reagent types scheduled to be combined with the one or more samples at the at least one testing time. The scheduling information may be received via LIS 824 and user interface 830.

The received information used to determine at least one testing time may include historical testing information. The historical testing information may include one or more previous times that a reagent type has been tested and test order information indicating one or more previous times that a reagent type has arrived at the system for testing.

The received information used to determine at least one testing time may include reagent location and storage information. For example, the reagent storage information may indicate an amount of each type of common reagent stored at the one or more local reagent storage areas and an amount of each type of uncommon reagent stored at the one or more central storage areas. The reagent location information may include one or more locations of each type of common reagent on the track and one or more locations of each type of uncommon reagent on the track. The received information used to determine at least one testing time may include testing station information indicating which testing station is configured to perform the one or more tests.

As shown at block 1108, the method may also include directing the one or more common reagents from the one or more local reagent storage areas 818 to the one or more testing stations 810 based on the received information. For example, control system 822 may receive scheduling information indicating that one or more of the more frequently performed tests (requiring one or more common reagents to be mixed with one or more samples) are scheduled for testing within a certain time interval (1:00 to 1:15) at testing station 810 at module 806. Control system 822 may also receive reagent information indicating that one or more common reagents needed for testing are stored at local reagent storage areas 818 at module 806. Control system 822 may then direct the one or more common reagents from the local reagent storage areas 818 at module 106 to the testing stations 810 at module 106 within the certain time interval (1:00 to 1:15).

As shown at block 1112, the method may also include performing one or more tests at the one or more testing stations. For example, control system 822 may cause the one or more frequently performed tests to be performed between 1:00 and 1:15 at testing station 810 at module 806 by combining the one or more common reagents with the one or more samples. Control system 822 may cause the frequently performed tests to be performed via one or more pick and place devices 832 at module 806 and/or one or more local controllers.

As shown at block 1110, the method may also include directing the one or more uncommon reagents from one or more central reagent storage areas, such as storage areas 820, to one or more testing stations 818 based on the received information. For example, control system 822 may receive historical information indicating that one or more of the less frequently performed tests (requiring one or more uncommon reagents to be mixed with one or more samples) at 3:00 for each of the last 10 days. Control system 822 may also receive reagent information indicating that the one or more uncommon reagents needed for testing are stored at central reagent storage areas 820. Control system 822 may also receive testing information indicating that testing station 810 at module 804 is capable of performing the less frequently performed tests. Control system 822 may then direct the one or more uncommon reagents from the central reagent storage areas 820 to the testing station 810 at module 804 at 3:00 for testing.

At block 1112, the method may also include performing the one or more less frequently performed tests at the one or more testing stations. For example, control system 822 may cause the one or more less frequently performed tests to be performed at testing station 810 at module 804 at 3:00 by combining the one or more uncommon reagents with the one or more samples. Control system 822 may cause the less frequently performed tests to be performed via one or more pick and place devices 832 located at module 804 and/or one or more local controllers.

The control system 822 may include one or more processors configured to receive instructions to perform any of the processes described in this document. In some embodiments, the instructions to perform any of the processes described in this document may be stored on a tangible computer readable medium.

Although the invention has been described with reference to exemplary embodiments, it is not limited thereto. Those skilled in the art will appreciate that numerous changes and modifications may be made to the preferred embodiments of the invention and that such changes and modifications may be made without departing from the true spirit of the invention. It is therefore intended that the appended claims be construed to cover all such equivalent variations as fall within the true spirit and scope of the invention.

What is claimed is:

1. An automation system for use with in vitro diagnostics comprising:
    a track configured to provide one or more paths;
    a plurality of carriers configured to move independently along the track, each of the plurality of carriers configured to hold at least one of: (i) one or more of a plurality of sample tubes; and (ii) one or more of a plurality of reagent packs containing reagents having reagent types;
    a plurality of local modules linked by the track, each of the plurality of modules comprising:
        one or more testing stations, each testing station configured to perform one or more tests by combining one or more reagents from the one or more reagent packs with a sample from the one or more sample tubes, and
        one or more local reagent storage areas located at or proximate to the one or more testing stations and configured to store the one or more reagent packs;
    one or more central reagent storage areas housed apart from the a plurality of local modules configured to store the one or more reagent packs and accessible to the a plurality of carriers; and
    a control system configured to: (i) direct the one or more reagent packs from the one or more local reagent storage areas to the one or more testing stations based on received reagent information; and (ii) direct the one or more reagent packs from the one or more central reagent storage areas to the one or more testing stations via the plurality of carriers based on the received reagent information.

2. The automation system of claim 1, wherein
    the one or more local reagent storage areas are configured to store one or more common reagents of the plurality of reagent packs,
    the one or more central reagent storage areas are configured to store one or more uncommon reagents of the plurality of reagent packs, and
    the control system is further configured to: (i) direct the one or more reagent packs having a common reagent type from the one or more local reagent storage areas to the one or more testing stations to perform the one or more tests based on received reagent information; and (ii) direct the one or more reagent packs having an uncommon reagent type from the one or more central reagent storage areas to the one or more testing stations to perform the one or more tests based on the received reagent information.

3. The automation system of claim 1, wherein the reagent information comprises scheduling information indicating at least one of: (i) an amount of the one or more reagent types scheduled to be combined with the one or more samples at one or more scheduled times; and (ii) an amount of the one or more reagent types scheduled to be combined with the one or more samples at the one or more testing stations.

4. The automation system of claim 3, wherein the scheduling information is received via a laboratory information system.

5. The automation system of claim 1, wherein the reagent information is received via a user interface.

6. The automation system of claim 1, wherein the control system is further configured to direct the one or more common reagent packs and the one or more uncommon reagent packs based on historical testing information.

7. The automation system of claim 1, wherein the control system is further configured to direct the one or more reagent packs having a common reagent type and the one or more reagent packs having an uncommon reagent type between: (i) the one or more local reagent storage areas; (ii) the one or more central reagent storage areas; and (iii) the testing stations to perform the one or more tests.

8. The automation system of claim 1, wherein the control system is further configured to direct the one or more reagent packs having a common reagent type to the one or more central reagent storage areas prior to directing the one or more reagent packs having the common reagent type to the one or more testing stations.

9. The automation system of claim 8, wherein the one or more local reagent storage areas comprise at least one long term local reagent storage area, and
    the control system is further configured to direct the one or more of the plurality of reagent packs from the one or more central storage areas to the at least one long term local reagent storage area prior to directing the one or more reagent packs to the one or more testing stations.

10. The automation system of claim 8, wherein the one or more local reagent storage areas comprise at least one short term local reagent storage area, and
    the control system is further configured to direct one or more of the plurality of reagent packs from the one or more central storage areas to the at least one short term local reagent storage area prior to directing the one or more reagent packs to the one or more testing stations.

11. The automation system of claim 1, wherein groups of the plurality of reagents are stored in the reagent packs, and
    the control system is further configured to: (i) direct one or more reagent packs having an uncommon reagent type from the one or more central reagent storage areas to the one or more testing stations to perform the one or more tests based on the received reagent information; and (ii) direct the one or more uncommon reagent type reagent packs having at least one uncommon reagent remaining in the respective one or more uncommon reagent type packs (a) back to the one or more central reagent storage areas after the one or more tests is performed or (b) to the one or more local reagent storage areas after the one or more tests is performed.

12. The automation system of claim 1, further comprising one or more pick and place devices for moving the plurality of sample tubes and the plurality of reagent packs between: (i) the one or more local reagent storage areas; (ii) the one or more central reagent storage areas; (iii) the testing stations to perform the one or more tests; and (iv) the track.

13. The automation system of claim 1, further comprising a reagent track configured to provide one or more reagent paths,
wherein the control system is further configured to: (i) direct the one or more sample tubes along the track; and (ii) direct the one or more reagent packs having a common reagent type and the one or more reagent packs having an uncommon reagent type along the reagent track.

14. The automation system of claim 1, wherein the control system is further configured to direct one or more of the plurality of reagent packs based on the received reagent information indicating at least one of: (i) an amount of each type of common reagent stored at the one or more local reagent storage areas; (ii) an amount of each type of uncommon reagent stored at the one or more central storage areas; (iii) one or more locations of each type of common reagent on the track; and (iv) one or more locations of each type of uncommon reagent on the track.

15. The automation system of claim 1, wherein the control system is further configured to direct one or more of the plurality of reagent packs based on testing information indicating which testing station is configured to perform the one or more tests.

16. The automation system of claim 1, wherein the control system is further configured to remove empty reagent packs from the track.

17. The automation system of claim 1, wherein the control system is further configured to direct empty packs from the one or more local reagent storage areas to the one or more central reagent storage areas.

18. An automation system for use with in vitro diagnostics comprising:
(I) a plurality of analyzers, each of the plurality of analyzers comprising:
(A) a track configured to provide one or more paths;
(B) a plurality of carriers configured to independently move along the track, each of the plurality of carriers configured to hold at least one of: (i) one or more of a plurality of sample tubes; and (ii) one or more of a plurality of reagent packs containing reagents having reagent types;
(C) a plurality of local modules, each of the local modules comprising:
(a) one or more testing stations configured to perform one or more tests by combining one or more reagents from the one or more reagent packs with a sample from the one or more sample tubes; and
(b) one or more local reagent storage areas located at or proximate to the one or more testing stations and configured to store one or more common reagents of the plurality of reagent packs;
(II) one or more central modules housed apart from the one or more local modules comprising one or more central reagent storage areas configured to store one or more uncommon reagents of the plurality of reagent packs; and
(III) a control system configured to: (i) direct the one or more common reagents from the one or more local reagent storage areas of each respective analyzer to the one or more testing stations of each respective analyzer to perform the one or more tests based on reagent information; and (ii) direct the one or more uncommon reagents from the one or more central reagent storage areas of each respective analyzer to the one or more testing stations of each respective analyzer via the plurality of carriers to perform the one or more tests based on the reagent information.

19. The automation system of claim 18, wherein the control system is configured to direct the one or more common reagents and the one or more uncommon reagents based on the reagent information received from at least one of: (i) the one or more analyzers; (ii) the one or more local modules; (iii) the one or more central modules; and (iv) one or more of the plurality of carriers.

20. The automation system of claim 18, further comprising a scheduling information storage device configured to store the reagent information indicating at least one of: (i) an amount of the one or more reagent types scheduled to be combined with the one or more samples at one or more scheduled times; and (ii) an amount of the one or more reagent types scheduled to be combined with the one or more samples at the one or more testing stations,
wherein the control system is configured to direct the one or more reagent packs having a common reagent type and the one or more reagent packs having an uncommon reagent type based on the stored reagent information.

21. The automation system of claim 18, further comprising one or more calibration systems configured to calibrate the one or more common reagents and the one or more uncommon reagents,
wherein the control system is further configured to direct the one or more reagent packs having a common reagent type and the one or more reagent packs having an uncommon reagent type to be calibrated by the one or more calibration systems at a predetermined time prior to their scheduled testing.

22. The automation system of claim 18, wherein one or more of the plurality of analyzers comprises a connecting track portion which connects the tracks of the one or more analyzers, and
wherein the control system is further configured to direct the reagent packs having a common reagent type and the one or more reagent packs having an uncommon reagent type between the one or more analyzers.

23. A method for operating an in vitro diagnostics system, comprising:
storing one or more common reagents of a plurality of reagents held in reagent packs at one or more local reagent storage areas located within each of a plurality of local modules at or proximate to one or more testing stations within each of the plurality of local modules;
storing one or more uncommon reagents of the plurality of reagents held in reagent packs at one or more central reagent storage areas housed apart from the a plurality of local modules;
receiving information used to determine at least one testing time at the one or more testing stations for one or more of the plurality of reagents to be combined with one or more samples;
directing the one or more reagent packs having a common reagent type from the one or more local reagent storage areas to the one or more testing stations via independently movable carriers based on the received information;

directing the one or more reagent packs having an uncommon reagent type from the one or more central reagent storage areas to the one or more testing stations via the independently movable carriers based on the received information; and performing at least one test at the one or more testing stations by combining at least one of: (i) the one or more common reagents with the one or more samples; and (ii) the one or more uncommon reagents with the one or more samples.

24. The method of claim 23, wherein the receiving information used to determine at least one testing time comprises receiving scheduling information indicating at least one of: (i) one or more reagent types scheduled to be combined with the one or more samples at the at least one scheduled testing time; and (ii) an amount of the one or more reagent types scheduled to be combined with the one or more samples at the at least one testing time.

25. The method of claim 23, wherein the receiving information used to determine at least one testing time comprises receiving historical testing information.

26. The method of claim 23, wherein the receiving information used to determine at least one testing time comprises receiving reagent information indicating at least one of: (i) an amount of each type of common reagent stored at the one or more local reagent storage areas; and (ii) an amount of each type of uncommon reagent stored at the one or more central storage areas.

27. The method of claim 23, further comprising directing the one or more reagent packs having an uncommon reagent type from the one or more central storage areas to the one or more local reagent storage areas prior to directing the one or more reagent packs having an uncommon reagent type to the one or more testing stations.

28. The method of claim 23, further comprising directing the one or more reagent packs having a common reagent type to the one or more central reagent storage areas prior to directing the one or more reagent packs having a common reagent type to the one or more testing stations.

* * * * *